United States Patent [19]
Truesdale et al.

[11] Patent Number: 5,877,469
[45] Date of Patent: Mar. 2, 1999

[54] APPARATUS FOR ELECTRICAL DESTRUCTION OF MEDICAL INSTRUMENTS

[75] Inventors: Richard S. Truesdale, Akron; Ronald L. Nowak, Chagrin Falls; Ronald J. Garcowski, Parma, all of Ohio

[73] Assignee: Innovative Medical Equipment, Inc., Clearwater, Fla.

[21] Appl. No.: 868,234

[22] Filed: Jun. 3, 1997

Related U.S. Application Data

[63] Continuation-in-part of Ser. No. 381,638, Jan. 31, 1995, Pat. No. 5,637,238.

[51] Int. Cl.⁶ .................................................. B23K 11/22
[52] U.S. Cl. .................................................... 219/68
[58] Field of Search .............................................. 219/68

[56] References Cited

U.S. PATENT DOCUMENTS

| | | | |
|---|---|---|---|
| 1,502,932 | 7/1924 | Young . | |
| 2,101,700 | 12/1937 | Chestnut, Jr. | 29/66 |
| 2,606,266 | 8/1952 | Duch et al. | 219/1 |
| 3,091,145 | 5/1963 | Manganelli | 83/184 |
| 3,469,750 | 9/1969 | Vanderbeck | 225/94 |
| 3,683,733 | 8/1972 | Johan et al. | 83/199 |
| 3,750,966 | 8/1973 | Anderson | 241/99 |
| 3,851,555 | 12/1974 | Eldridge et al. | 83/165 |
| 3,929,295 | 12/1975 | Montalbano | 241/190 |
| 3,958,765 | 5/1976 | Musselman | 241/99 |
| 4,040,425 | 8/1977 | Goodling et al. | 128/303.14 |
| 4,205,794 | 6/1980 | Horton et al. | 241/73 |
| 4,255,996 | 3/1981 | Choksi et al. | 83/140 |
| 4,275,628 | 6/1981 | Greenhouse | 83/167 |
| 4,315,448 | 2/1982 | Ball | 83/167 |
| 4,404,881 | 9/1983 | Hanifl | 83/167 |
| 4,447,694 | 5/1984 | Brochier et al. | 219/68 |
| 4,531,437 | 7/1985 | Szablak et al. | 83/165 |
| 4,628,169 | 12/1986 | Ch'ing-Lung | 219/68 |
| 4,877,934 | 10/1989 | Spinello | 219/68 |
| 4,905,916 | 3/1990 | Sorwick et al. | 241/23 |
| 4,961,541 | 10/1990 | Hashimoto | 241/65 |
| 4,965,426 | 10/1990 | Colombo | 219/68 |
| 5,076,178 | 12/1991 | Kohl et al. | 110/250 |
| 5,138,124 | 8/1992 | Kirk et al. | 219/68 |
| 5,147,304 | 9/1992 | Fladung | 604/110 |
| 5,212,362 | 5/1993 | Burden et al. | 219/68 |
| 5,245,935 | 9/1993 | Fukuda | 110/250 |
| 5,268,549 | 12/1993 | Butler | 219/68 |
| 5,282,428 | 2/1994 | Greville et al. | 110/250 |
| 5,300,752 | 4/1994 | Elmerick et al. | 219/68 |
| 5,329,087 | 7/1994 | Kohl et al. | 219/68 |
| 5,336,862 | 8/1994 | Yelvington | 219/68 |
| 5,391,849 | 2/1995 | Furuya et al. | 219/68 |
| 5,540,416 | 7/1996 | Huang | 219/68 |
| 5,551,355 | 9/1996 | Haines et al. | 219/68 |
| 5,736,706 | 4/1998 | Butler | 219/68 |
| 5,741,230 | 4/1998 | Miller | 219/68 |

FOREIGN PATENT DOCUMENTS

| | | |
|---|---|---|
| 2 273 231 A | 12/1992 | United Kingdom . |
| WO 96/23538 | 8/1996 | WIPO . |

*Primary Examiner*—Geoffrey S. Evans
*Attorney, Agent, or Firm*—Renner, Kenner, Greive Bobak, Taylor & Weber

[57] ABSTRACT

A hypodermic needle destruction system that utilizes a primary sub-housing with a cartridge demountably secured to the primary sub-housing. First and second electrodes are disposed within the cartridge. A guide is incorporated in the cartridge for accepting a metallic medical instrument for destruction. The guide directs the metallic medical instrument such that insertion thereof into and at least partially through the guide effects an electrical connection between the first and second electrodes. At least one of the electrodes is movable with respect to the other, and a sufficient level of electrical energy is applied across the first and second electrodes to cause the electrical destruction of the medical instrument positioned in electrical contact across the first and second electrodes. A variety of sub-housing alternatives as well as a variety of electrode and protective cap assemblies are disclosed.

22 Claims, 27 Drawing Sheets

APPARATUS FOR ELECTRICAL DESTRUCTION OF MEDICAL INSTRUMENTS

RELATED APPLICATION

The present application is a continuation-in-part of U.S. application, Ser. No. 08/381,638, filed on Jan. 31, 1995, which issued as U.S. Pat. No. 5,637,238 on Jun. 10, 1997.

TECHNICAL FIELD

The present invention relates generally to an apparatus for the destruction of metallic medical instruments by using electrical energy. More particularly, the present invention relates to an apparatus that electrically reduces the metallic, medical instrument to swarf. Specifically, the present invention relates to the destruction of medical instruments such as hypodermic needles by passing electrical energy through the instruments for which disposal is desired as the instrument spans two electrodes at least one of which oscillates, or reciprocates, with respect to the other.

BACKGROUND OF THE INVENTION

One of the more important activities for medical safety is the disposal of used medical instruments, and particularly disposable, metallic, hypodermic needles. Disposable hypodermic needles are widely used in hospitals and other medical facilities to draw body fluids from, and to inject medications into, patients. These needles are made disposable because of the difficulties, and inefficiencies, involved in sterilizing and sharpening hypodermic needles for reuse. Inasmuch as the needles are intended to be discarded after use, a problem arises as to their safe post-use storage and disposal.

In virtually every state it is illegal to discard used hypodermic needles as ordinary waste inasmuch as their sharp points, as well as the disease organisms carried on such needles, may injure hospital and/or waste disposal personnel. Moreover, there is also the very important need to prevent the disposed needles from being used by others, either recklessly or for illegal purposes. Because the current state of the art relating to the destruction of hypodermic needles is so unsatisfactory, untold quantities of such medical instruments are not being destroyed after use but are being illegally foisted on the enviromnent, with disastrous results.

Many systems and apparatus, both mechanical and electrical, have been proposed over the years, but the prior proposals have each been deemed to be unsatisfactory.

For example, the prior known mechanical systems for hypodermic needle destruction have simply either crushed or broken the needles. Although these devices do prevent the reuse of the needles, such devices often serve to multiply the number of sharp points available inadvertently to pierce unwary humans. In addition, such disposal does not, in any way, neutralize any body fluids inadvertently retained on, or in, the needles. One example of such an arrangement is disclosed in U.S. Pat. No. 4,531,437 issued on Jul. 30, 1985.

In order to attempt to neutralize the body fluids retained in, or on, the needles, as well as any disease organisms present in those fluids, incineration of the disposable needles has also been utilized. Bulk incineration of accumulated needles, however, poses the continued threat of injury during that period of time beginning immediately following their usage and extending until the needles are actually received in the incinerator. Moreover, if the incinerating temperature is not sufficient to destroy the needle it continues to be a hazard, an unfortunate situation that has occurred in the past.

The period of potential exposure to needles that are contaminated has been reduced by supplying portable devices that are available to incinerate the needles electrically immediately after they have been used. The prior known electrical systems generally use electrical resistance heating to incinerate the needle. These systems have used both stationary electrodes, or relatively movable electrodes. One form of the movable electrode systems encompass arrangements wherein the needle is moved relative to the electrode, such as disclosed in U.S. Pat. No. 4,877,934, issued Oct. 31, 1989. In other forms of the movable electrode systems one of the electrodes is rotated relative to the needle, such as disclosed in U.S. Pat. No. 5,138,124, issued on Aug. 11, 1992. Heretofore, movable electrode systems, without further processing of the needle, leave at least one portion of the needle with a sharp end, even after the needle has been significantly destroyed.

The stationary electrode systems, such as that shown in U.S. Pat. No. 4,965,426 issued Oct. 23, 1990, are similar to the movable electrode systems currently in use. However, these systems generally do not destroy as much of the overall length of the needle as the movable systems do. These systems rely on the melting process to leave a rounded end, and thus do not assure the operator that the end is indeed blunt.

Even in the most advanced of the prior known systems the swarf must eventually be emptied, and most workers are fearful of having to open the apparatus to empty the residue. Even though they know that the swarf does not contain sharp points, they are fearful of inhaling any dust that might become airborne during the emptying process.

Careful attention has also disclosed that users of the electrical disposal devices are fearful of any gaseous vapor, or electrical sparks, escaping back into the atmosphere during operation of such devices.

It is thus apparent that a need remains for an improved method and apparatus for destroying metallic, medical instruments, and particularly hypodermic needles, in a more effective and efficient manner. The present invention is directed to that objective.

SUMMARY OF THE INVENTION

It is, therefore, a primary object of the present invention to provide a novel disposal system for metallic, medical instruments, such as hypodermic needles, wherein any remaining stub is blunted.

It is another object of the present invention to provide a novel disposal system for metallic, medical instruments, as above, wherein any body fluids inadvertently retained on, or in, the needles—as well as any disease organism carried by those fluids—is neutralized.

It is a further object of the present invention to provide a novel disposal system for metallic, medical instruments, as above, wherein the instrument to be destroyed spans two electrodes at least one of which oscillates, or reciprocates, with respect to the other.

It is yet another object of the present invention to provide a novel disposal system for metallic, medical instruments, as above, wherein the swarf resulting from the destruction of the medical instruments and any body fluid which is injected into the apparatus prior to neutralization are retained in a cartridge that can itself be destroyed without opening.

It is yet a further object of the present invention to provide a novel disposal system for metallic, medical instruments, as above, wherein gaseous vapor, or electrical sparks, are precluded from escaping back into the atmosphere during operation of the device.

It is a still further object of the present invention to provide a novel disposal system for metallic, medical instruments, as above, wherein the control functions may be accomplished with a low energy, electrical circuit and destruction of the needle may be accomplished with a high energy, electrical circuit.

It is an even further object of the present invention to provide a novel disposal system for metallic, medical instruments, as above, wherein the pair of spaced, relatively reciprocating electrodes are utilized to respond to the placement of a metallic, medical instrument thereacross to activate both electrical circuits.

These and other objects of the invention, as well as the advantages thereof over existing and prior art forms, which will be apparent in view of the following detailed specification, are accomplished by means hereinafter described and claimed.

In general, a disposal system embodying the concepts of the present invention utilizes a primary sub-housing with a cartridge demountably secured to the primary sub-housing. First and second electrodes are disposed within the cartridge. A guide means is incorporated in one of the electrodes for accepting a metallic, medical instrument for destruction. The guide means directs the metallic, medical instrument such that insertion thereof in the guide means effects an electrical connection between the first and second electrodes. At least one of the electrodes oscillates with respect to the other, and a sufficient level of electrical energy is applied across the first and second electrodes to cause the electrical destruction of the metallic, medical instrument positioned in electrical contact across the first and second electrodes.

While systems utilizing a single electrical system are convenient, it is much more economical and efficient to use two, inter-related electrical power systems which provide two discrete electrical energy levels, and the present invention provides such a system.

Both the low and the high energy electrical systems are activated by needle insertion. The high energy electrical system is operable to supply the power necessary to: destroy the metallic, medical instrument; to operate a fan; and, to cause at least one of the electrodes to move within a reciprocating path. After the metallic, medical instrument is fully destroyed, the electrodes will, after a predetermined period of time, turn off both the high and the low electrical energy systems.

To acquaint persons skilled in the arts most closely related to the present invention, one preferred embodiment of an electrical disposal system for medical instruments that illustrates a best mode now contemplated for putting the invention into practice is described herein by, and with reference to, the annexed drawings that form a part of the specification. The exemplary disposal system is described in detail without attempting to show all of the various forms and modification in which the invention might be embodied. As such, the embodiment shown and described herein is illustrative, and as will become apparent to those skilled in these arts can be modified in numerous ways within the spirit and scope of the invention; the invention being measured by the appended claims and not by the details of the specification.

DESCRIPTION OF AN EXEMPLARY EMBODIMENT

One representative form of an apparatus adapted for the electrical destruction of medical instruments, and embodying the concepts of the present invention, is designated generally by the numeral 10 on the accompanying drawings. The representative apparatus 10 is particularly adapted for the destruction of hypodermic needles, but as will become apparent, the apparatus 10 may be adapted for the destruction of a wide variety of metallic, medical instruments. Even so, the following description will, for the convenience of the reader, be specifically directed to hypodermic needles, although it is to be understood that the concepts of the present invention are readily adaptable to a wide variety of metallic, medical instruments.

Figure 1:
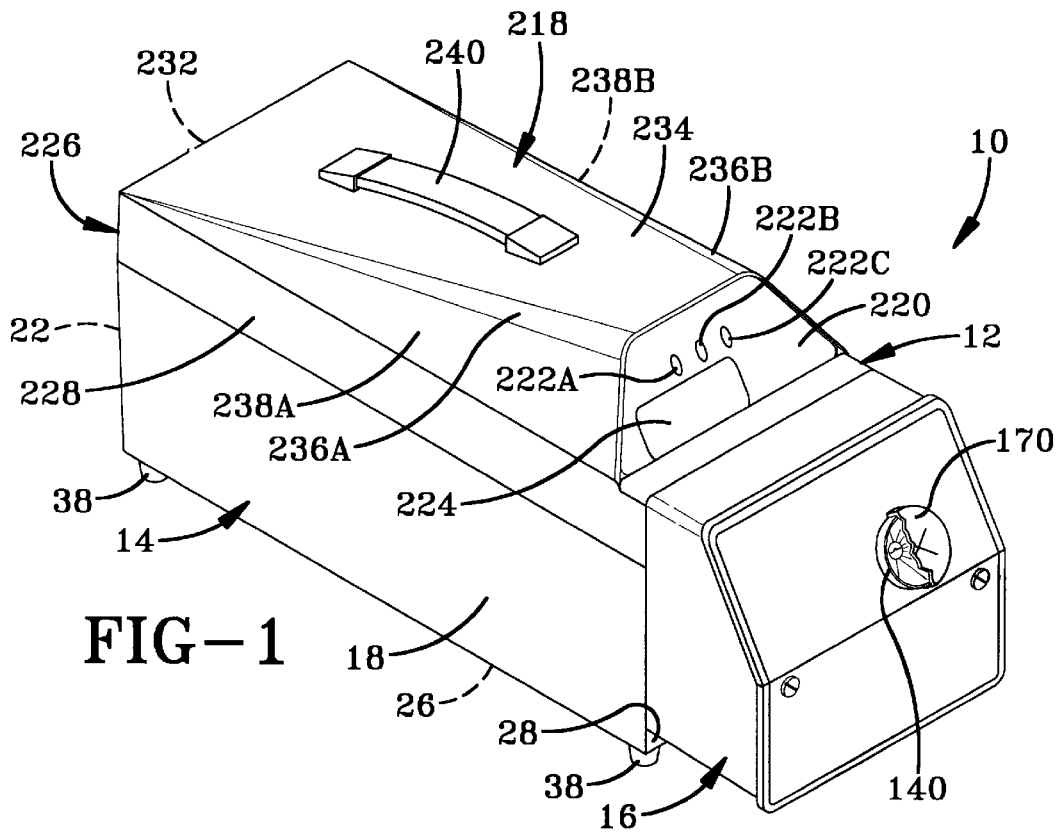
FIG. 1 is a frontal perspective of an apparatus incorporating the concepts of the present invention.
Figure 2:
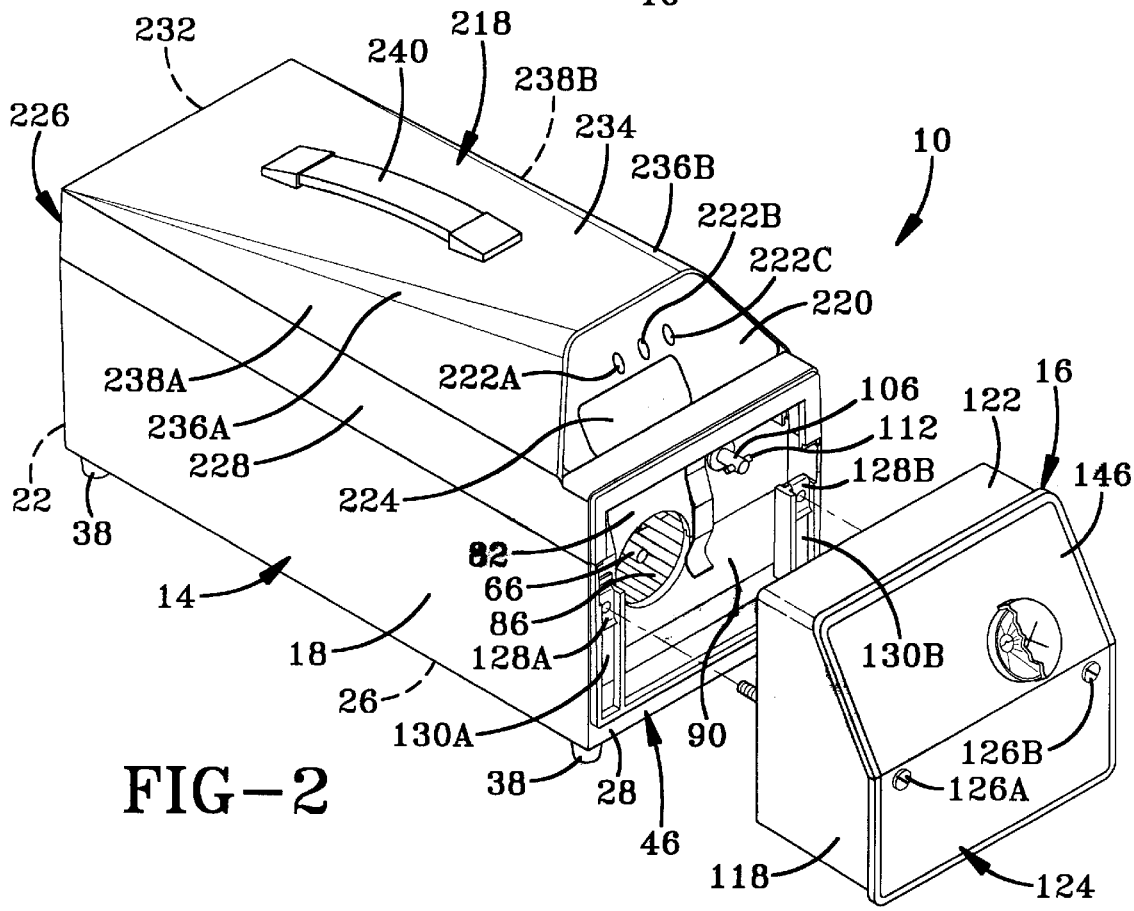
FIG. 2 is a view similar to FIG. 1, but exploded to depict the separability of the cartridge sub-housing from the primary sub-housing.

As seen in FIGS. 1 and 2, the overall housing 12 for the apparatus is divided into a primary sub-housing 14, and an associated sub-housing in the nature of a disposable, swarf-collecting, fluid-retaining cartridge that is demountably secured to the primary sub-housing 14. The cartridge sub-housing is designated by the numeral 16.

Figure 3:
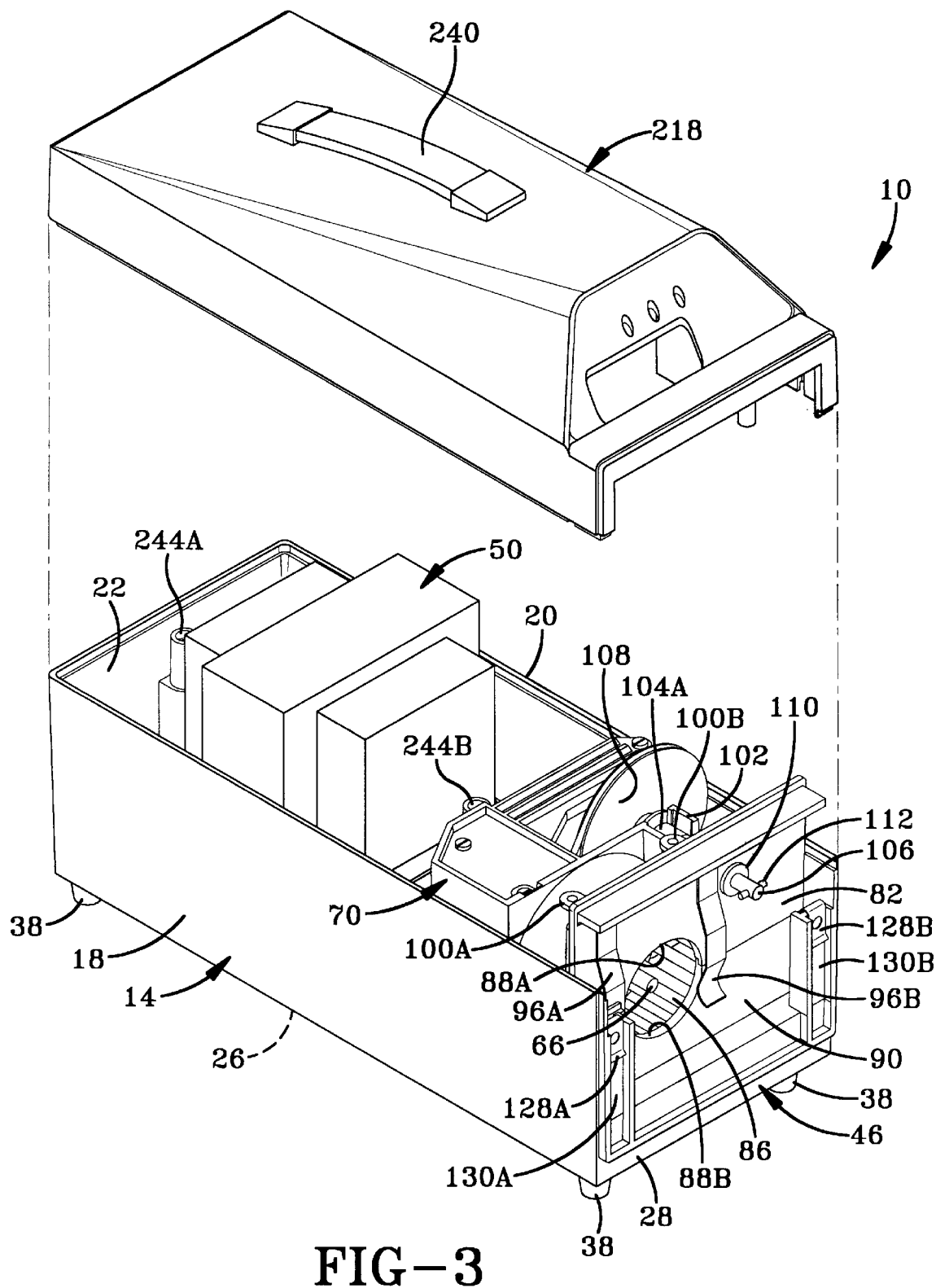
FIG. 3 is also a view similar to FIG. 1, but without depicting the cartridge sub-housing, and exploded to reveal the inter-relation of the cover with respect to the primary sub-housing.
Figure 4:
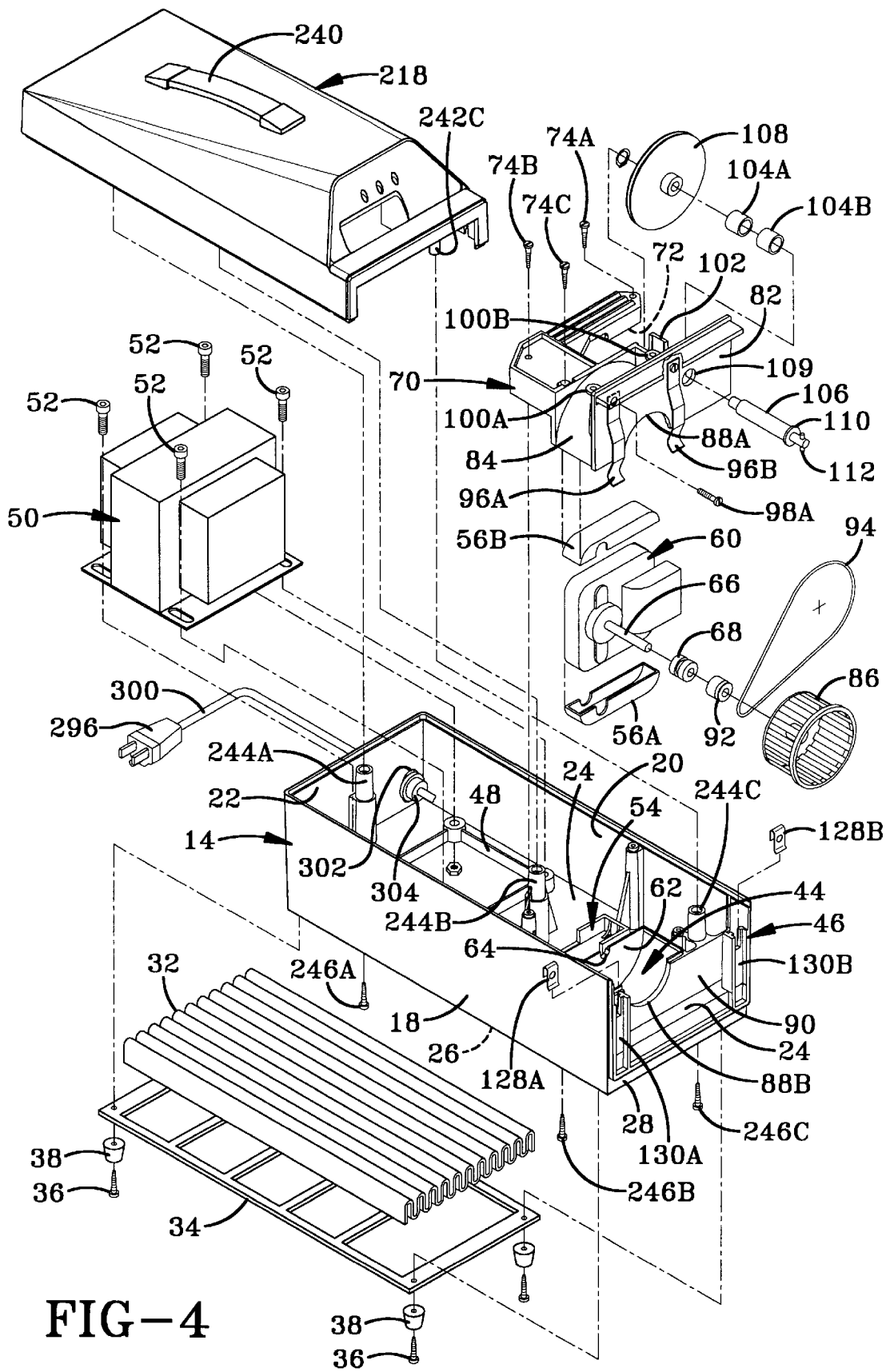
FIG. 4 is an exploded perspective of the primary sub-housing and the components operably received therein.

As best seen in FIGS. 3 through 6, the primary sub-housing 14 has laterally spaced side walls 18 and 20, an end, or rear, wall 22 and a base 24 that is offset upwardly from the lower edge 26 of the primary sub-housing 14—the lower edge 26 being collectively defined by the lower edges of the peripheral walls 18, 20 and 22 as well as the lip 28 that extends downwardly at the front of the primary sub-housing 12. The upwardly offset location of the base 24 may define a recess 30 on the underside of the primary sub-housing 14 that is adapted to receive an environment-protecting filter 32 which may be secured within the recess 30 by a retaining grille 34. As best seen in FIG. 4, the retaining grille 34 may be secured to the primary sub-housing 14 by a plurality of fastening means, such as the self-threading screws, 36. Non-skid feet 38 may also be appropriately secured to the primary sub-housing 14 by the screws 36. As will be hereinafter more fully explained, the environmental filter 32 may be eliminated if the cartridge sub-housing 16 is itself fully filtered.

Figure 5:
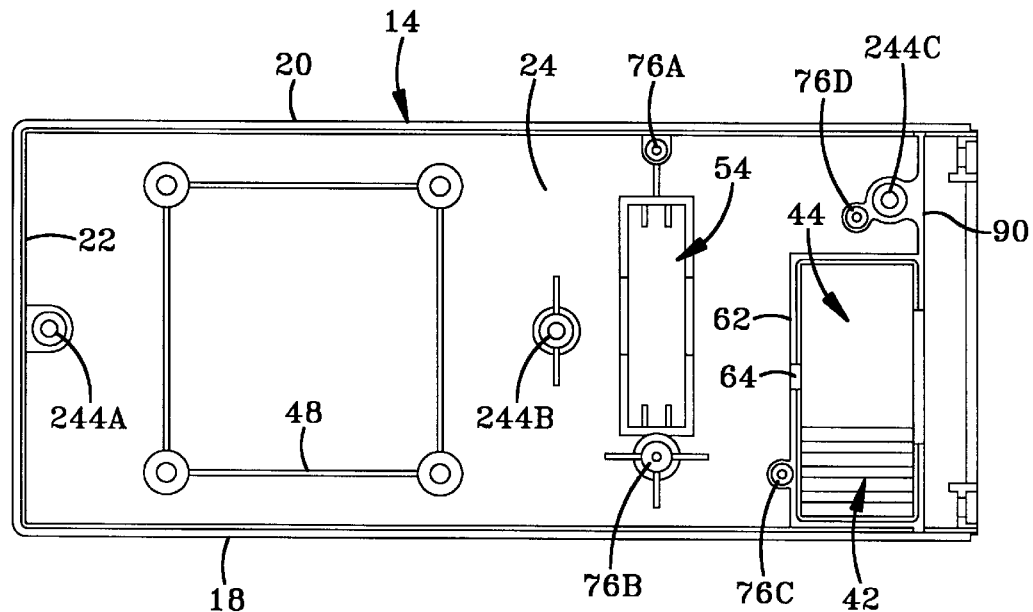
FIG. 5 is an enlarged top plan of the primary sub-housing, with all the internal components removed.
Figure 6:
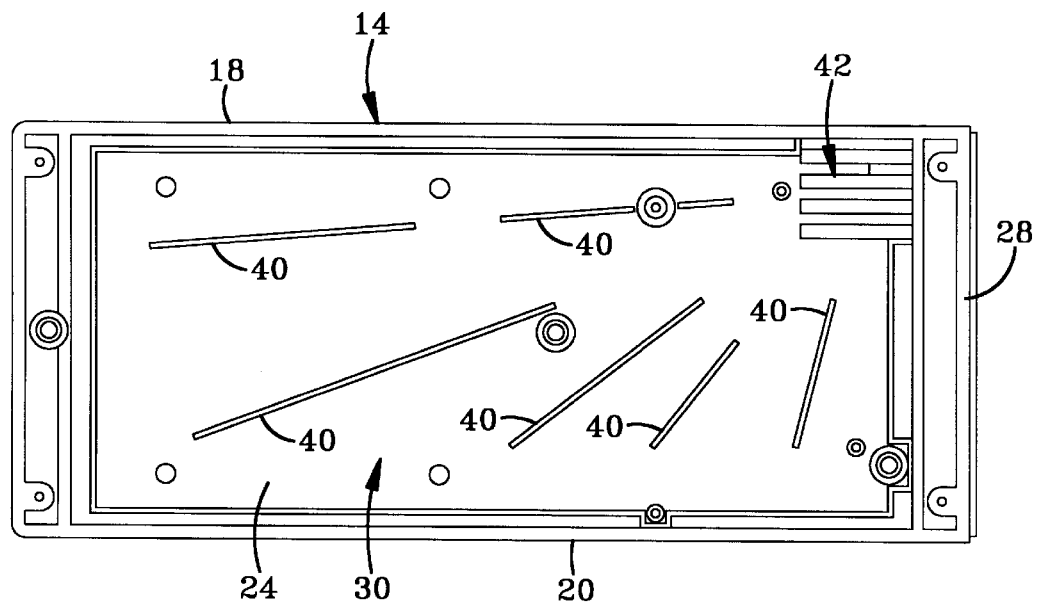
FIG. 6 is a bottom plan view of the primary sub-housing with the internal components removed, and drawn to the same scale as FIG. 5.
Figure 9:
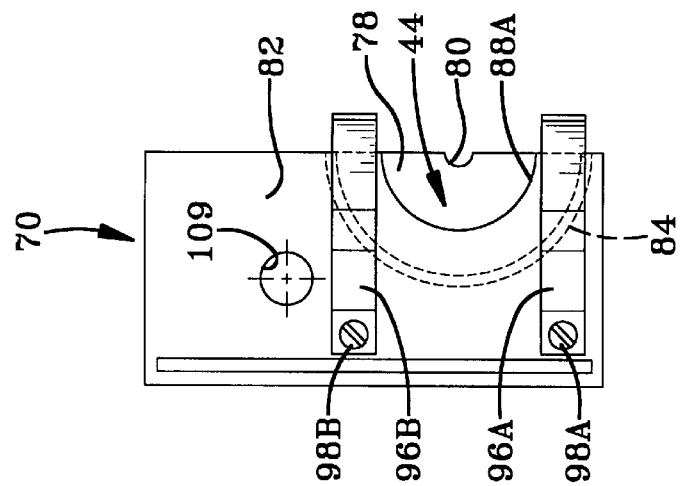
FIG. 9 is a frontal elevation of the mounting block taken substantially along line 9—9 of FIG. 7.
Figure 7:
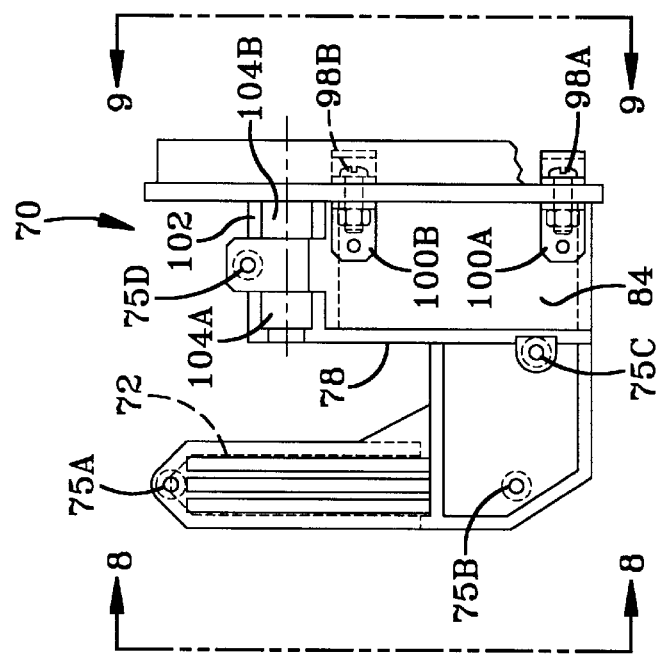
FIG. 7 is a top plan view of the mounting block utilized interiorly of the primary sub-housing.
Figure 8:
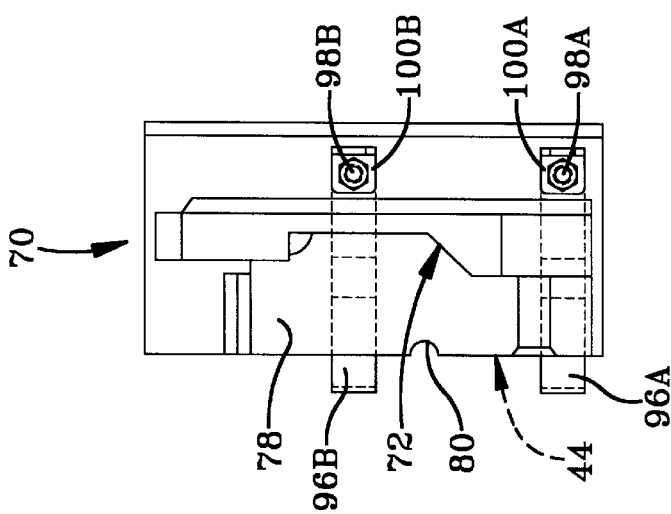
FIG. 8 is a rear elevation of the mounting block taken substantially along line 8—8 of FIG. 7.

The base 24 may, as shown in FIG. 6, be provided with a plurality of spacing ribs 40 that extend in a generally radial fashion outwardly from a grilled aperture 42 through which a fan-receiving chamber 44 (FIGS. 4 and 5) communicates with the recess 30. As such, the spacing ribs 40 permit the free flow of air within that portion of the recess 30 between the base 24 and the filter 32. This permits free access of the air entering the recess 30 through the grilled aperture 42 to the full surface of the filter 32. The environmental protecting filter 32 serves primarily to preclude the emission of aerosols, whether toxic or not, from the interior of the apparatus 10. Depending, therefore, on the use to which the particular needles to be disposed had been put, it might be sufficient to employ a high efficiency aerosol particulate filter 32 capable of a 99.97% dioctylphalate (DOP) efficiency for removing particulate as small as 0.3 microns (commercially available as a HEPA filter). On the other hand, for some installations it may be necessary to employ a aerosol particulate filter 32 capable of a 99.998% DOP efficiency for removing particulate matter as small as 0.1 microns (commercially available as an ULPA filter).

With continued reference to FIGS. 4 and 5, that surface of the base 24 which faces the interior of the primary sub-housing 14 may present a rectangular mounting pedestal 48 (also best seen in FIGS. 4 and 5) on which a multi-tap transformer 50 may be secured, as by four nut and bolt combinations 52. Forwardly of the mounting pedestal 48 the base 24 presents a raised edge, motor-mounting recess 54 that may receive a first vibration damper 56A (FIG. 4). The first vibration damper 56A is formed to encase that portion of a motor 60 which is received within the recess 54. A chamber wall 62 is disposed forwardly of the motor-mounting recess 54 to define the rearmost boundary of the fan-receiving chamber 44, and the chamber wall 62 may have a notch 64 that rotatably receives the motor shaft 66. A bearing member 68 is preferably received within the notch 64 to provide not only a low friction support for the shaft 66 but also to seal the fan-receiving chamber 44 from the remainder of the primary sub-housing 14.

As previewed in the previous paragraph, and as will appear in the detailed description which follows, a particular structural member, component or arrangement may be employed at more than one location. When referring generally to that type of structural member, component or arrangement a common numerical designation shall be employed. However, when one of the structural members, components or arrangements so identified is to be individually identified it shall be referenced by virtue of a letter suffix employed in combination with the numerical designation employed for general identification of that structural member, component or arrangement. Thus, there are at least two vibrations dampers which are generally identified by the numeral 56, but the specific, individual vibration dampers are, therefore, identified as 56A and 56B in the specification and on the drawings. This same suffix convention shall be employed throughout the specification.

A generally U-shaped, mounting block 70 (FIGS. 4 and 7 through 9) may be selectively secured within the primary sub-housing 14, and the mounting block 70 presents a motor-mounting recess 72 that is disposed in opposition to the motor-mounting recess 54 presented from the base 24 of the primary sub-housing 14. A second vibration damper 56B may be received in the recess 72 such that when the mounting block 70 is secured to the sub-housing 14—as by the four self-threading screws 74 which extend through bores 75A through 75D to engage the opposed stand-offs 76A through 76D, respectively (as shown in FIG. 5)—the vibration dampers 56A and 56B will capture the motor 60 therebetween. The mounting block 70 also includes a chamber wall 78 that is opposed to the chamber wall 62 and defines one side of the fan-receiving chamber 44 when the mounting block 70 is operably secured within the primary sub-housing 12. The chamber wall 78 may also have a notch 80 that rotatably receives the motor shaft 66. The bearing member 68 would, therefore, be received within the cylindrical aperture formed by the opposed notches 64 and 80 to provide a support for the shaft 66 and also to complete the seal between the fan-receiving chamber 44 and the remainder of the primary sub-housing 14.

The mounting block 70 also has a second wall 82 that is longitudinally spaced forwardly from the first wall 78, and an arcuate chamber wall 84 extends longitudinally therebetween to complete the definition of the fan-receiving chamber 44. An annular fan member 86 is received within the chamber 44 to be operatively connected to, and driven by, the shaft 66 of the motor 60. The second wall 82 has a semi-cylindrical aperture 88A that is opposed to a semi-cylindrical aperture 88B in an opposed transverse wall 90 that extends upwardly from the base 24 and laterally between the side walls 18 and 20 of the primary sub-housing 14. The opposed semi-cylindrical apertures 88A and 88B will, as will hereinafter become more apparent, constitute the intake to the fan-receiving chamber 44.

A drive pulley 92 (FIG. 4) is secured to that portion of the shaft 66 which extends between the motor 60 and the opposed walls 62 and 78. A drive belt 94 engages the pulley 92 for a purpose more fully hereinafter described.

A pair of resilient, electrical contact bars 96A and 96B are mounted in laterally spaced relation to overlie a portion of the second wall 82. By judicious selection of the lateral spacing, the contact bars 96A and 96B will be respectively positioned, with one on each side of the intake to the chamber 44 formed by the semi-cylindrical apertures 88A and 88B. The separate nut and bolt combinations 98A and 98B, respectively, by which the contact bars 96A and 96B are secured to the mounting block 70 may also each receive an electrical spade connector 100 by which to effect an electrical connection between the transformer and the nut and bolt combinations 98. That is, a spade connector 100A may be secured by nut and bolt combination 98A, and a spade connector 100B may be secured by nut and bolt combination 98B.

A bearing support 102 extends rearwardly from the wall 82 to receive the sleeve bearings 104 that stabilizes an electrode drive shaft 106. As shown, two axially spaced bearings 104A and 104B may be employed. A driven pulley 108 may be secured to the longitudinally rearward end portion of the electrode drive shaft 106. The driven pulley 108 is aligned with the drive pulley 92 to receive the drive belt 94. To slow the rotation of the electrode drive shaft 106 relative to the rotation of the motor shaft 66, it may be desirable to provide a diametral differential between the drive and driven pulleys 92 and 108, respectively, on the order of about 5-to-1.

The longitudinally forward end portion of the electrode drive shaft 106 extends through an aperture 109 in the wall 82 to present a stop which may comprise a shoulder formed directly on the shaft 106 or which may be effected by a washer 110, as depicted. An engaging dog 112 extends radially outwardly from one or both sides of the electrode drive shaft 106 for a purpose more fully hereinafter described.

As best seen in FIGS. 10 through 14, the swarf-collecting, fluid-retaining cartridge, or sub-housing, 16 is demountably secured to the open front 46 of the primary sub-housing 14, and upwardly of the lip 28, by means also hereinafter more fully described. The cartridge 16 itself has a base wall 114, a rear wall 116, laterally spaced side walls 118 and 120, a top wall 122 and a front wall 124 that is only removable when the cartridge 16 is not mounted on the primary sub-housing 14.

The cartridge 16 is demountably attachable to the primary sub-housing 14 as by the connecting means in the nature of machine-type screws 126A and 126B that extend through the cartridge 16 to be received in what are commonly referred to as Tinnerman nuts 128A and 128B that are supported from boxed flanges 130A and 130B located adjacent the respective side walls 18 and 20 of the primary sub-housing 14, as best seen in FIGS. 2 through 4. Preferably, the head 127 of each screw 126 should be designed to receive a unique tool so that only authorized personnel may remove the cartridge from the primary sub-housing 14.

To ensure that the pathway for the connecting means 126 will not provide any undesired access to, or from, the interior of the cartridge 16, closed first races 132A and 132B extend along the interior face of the respective side walls 118 and 120 of the cartridge 16. Second races 134A through 134D also extend along the respective side walls 118 and 120. The second races 134 receive the fastening means, such as by a plurality of self-threading screws 136, by which the front wall 124 is demountably attached to the remainder of the cartridge 16. Preferably, the head 137 of each screw 136 should also be designed to receive a unique tool so that only authorized personnel may remove the front wall 124 of the cartridge 16.

The cartridge 16 houses a fixedly positioned, non-movable, first electrode 140 and a uniquely movable, second electrode 142. The fixed electrode 140 is received within an opening 144 that penetrates the sloping portion 146 of the front wall 124. The fixedly positioned, first electrode 140 is mounted within the opening 144, as by a bowed snap ring 148 that is receivable within an annular recess 150 in the body portion 152 of the fixedly positioned, first electrode 140. As such, the snap ring 148 clamps the sloping portion 146 of the front wall 124 against a shoulder 154 on the body portion 152 of the fixed electrode 140.

Figure 15:
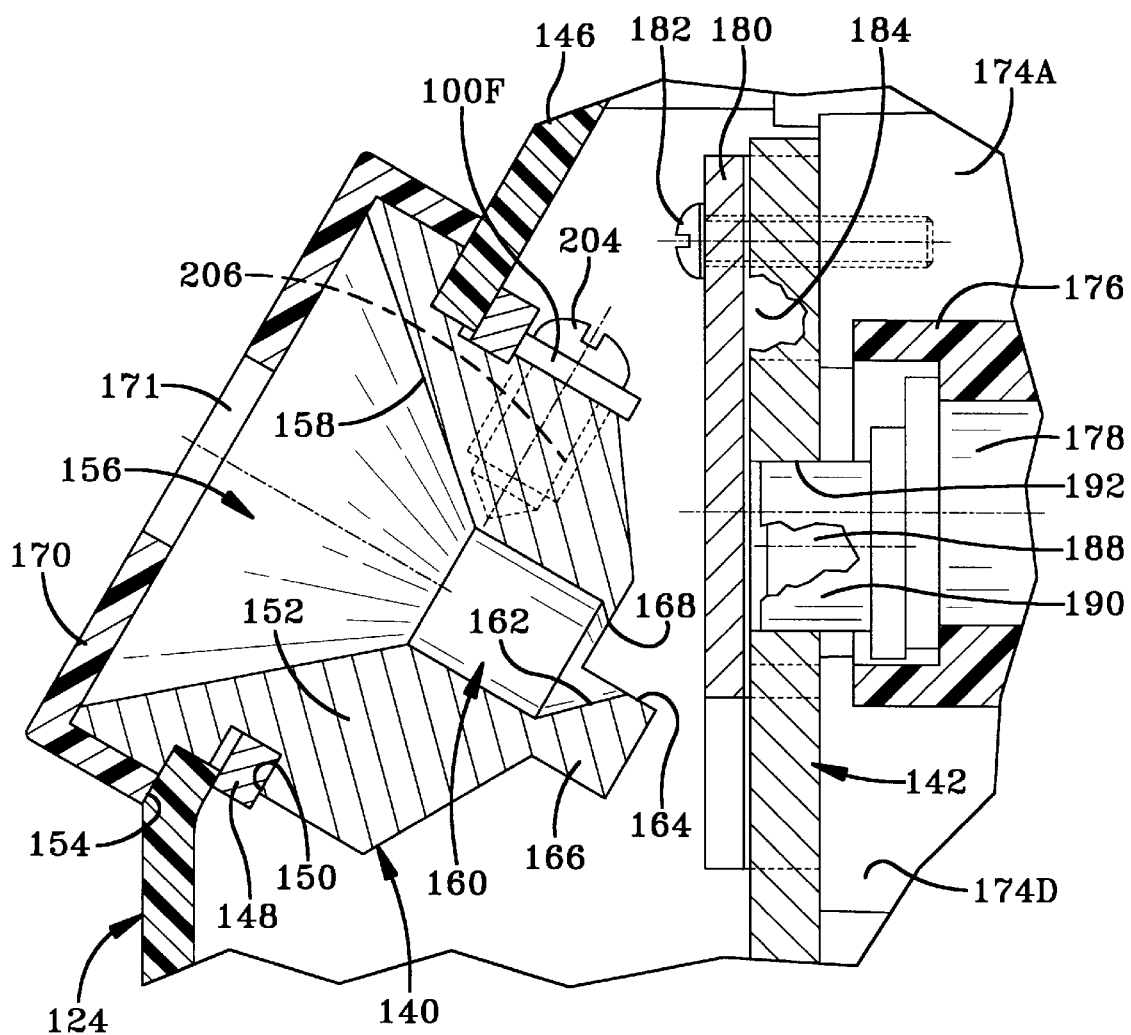
FIG. 15 is an enlarged portion of FIG. 14—the outline of the enlarged portion being delineated by the chain-line identified as "FIG-15" on FIG. 14.
Figure 16:
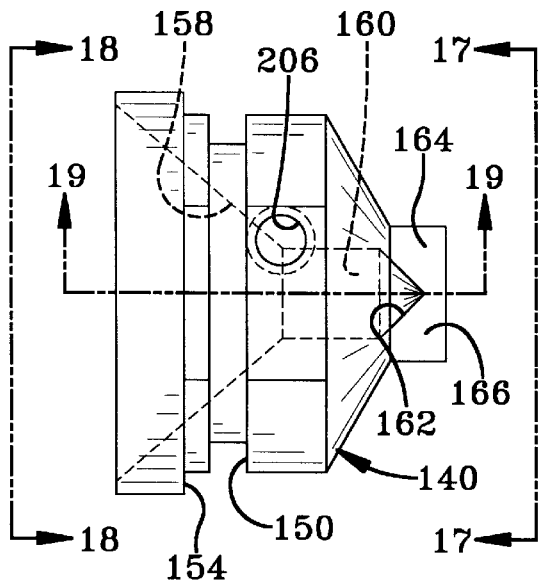
FIG. 16 is a side elevation of the fixed electrode that is depicted in cross-section in FIG. 15.
Figure 17:
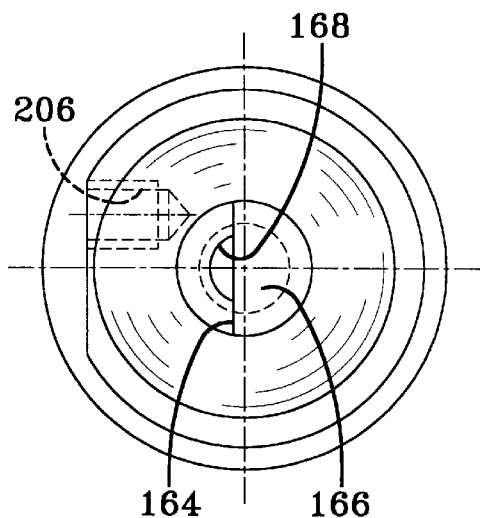
FIG. 17 is an end elevation taken substantially along line 17—17 of FIG. 16.
Figure 18:
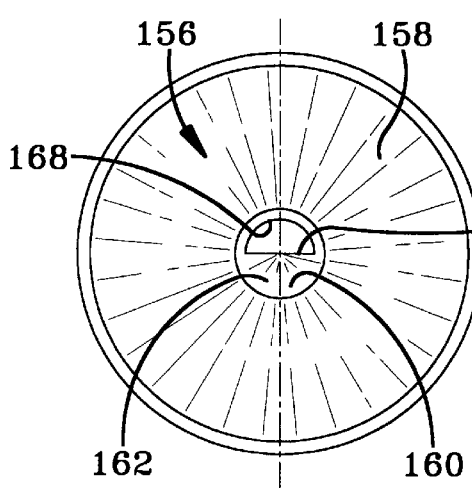
FIG. 18 is an end elevation taken substantially along line 18—18 of FIG. 64.

The fixedly positioned, first electrode 140 has a central opening 156 (FIG. 15) with an axially outermost, first, conical portion 158 that converges axially inwardly to merge into a cylindrical passage 160. The cylindrical passage 160 extends between the first, conically converging portion 158 and a second, conical portion 162 that converges to the chordal wall 164 of a deflecting terminus 166. The chordal wall 164 disposed in axially offset opposition to a semi-cylindrical rim 168 such that the generally opposed, but axially spaced, wall 164 and rim 168 impart stability to the medical instrument located therebetween as it engages the linearly reciprocating electrode 142. The diameter of the cylindrical passage 160 is chosen so that it will closely encase the needle insertably received therein in order to minimize the available space through which any sparks must travel to reach the exterior of the cartridge 16. On the other hand there must be a sufficient clearance between the needle and the cylindrical passage 160 in order to permit air to enter the cartridge in response to the action of the fan member 86.

A protective cap 170 that presents a flexible, slotted face 171 may be frictionally received over that portion of the fixed electrode 140 located on the outside of the front cover wall 124 to allow facile entry of a needle and environmental air drawn in by the fan member 86 but at the same time to preclude the escape of any sparks that are engendered by destruction of the needle against the linearly reciprocating electrode 142.

The second electrode 142 is mounted on the rear wall 116 of the cartridge 16 for movement between fixed limits. Specifically, the second electrode 142 may be in the form of a rectangular plate that is balanced across the edges of two, spaced, locating walls 172A and 172B. Locating wall 172A extends between stand-offs 174A and 174B, and locating wall 172B extends between stand-offs 174C and 174D. The stand-offs 174 may, as depicted, be located in a square matrix around an annular extension 176 within which a transfer shaft 178 is rotatably received. A guide plate 180 is mounted on the four stand offs 174 by a plurality of self-threading screws 182, and the guide plate 180 has a slideway 184 recessed into the rear face thereof to receive the second electrode 142.

The end of the rear portion of the transfer shaft 178 is bifurcated, as at 186, to engage the dog 112 on the electrode drive shaft 106. The frontal portion of the transfer shaft 178 terminates in an eccentrically located drive pin 188 that receives a dielectric bushing 190 that electrically insulates the transfer shaft 178 from the second electrode 142. The eccentric drive pin 188, on which the dielectric bushing 190 is mounted, is received within a laterally extending slot 192 in the second electrode 142. Thus, rotation of the transfer shaft 178 effects oscillating and reciprocating movement of the second electrode 142 between fixed limits. It should be understood that if the eccentricity of the drive pin 188 relative to the rotational axis of the transfer shaft 178 is minimized, the oscillation will appear to pulse, or vibrate. The rate of the periodic motion can, of course, be preselected by careful selection of the relative diameters of the drive pulley 92 and the driven pulley 108. In the preferred form of the invention the reciprocation is linear, and, in fact, constitutes a translational movement wherein all points on the moving electrode 142 will have, at any instant, the same velocity and direction of motion. Even though the preferred movement of the electrode 142 is translational linear reciprocation those skilled in the art can, therefore, select the specific oscillation, vibration or reciprocation desired for their purposes.

The rear wall 116 of the cartridge 16 is also provided with a grilled port 194 that aligns with the input to the fan-receiving chamber 44—the input being formed by the apertures 88A and 88B. The grilled port 194 is covered with a second filter 196. The second filter 196 is preferably a carbon filter which may be held in place by a removable grille 198 that may be mounted to the rear wall 116 of the cartridge 16 by two electrically conductive nut and bolt combination 200A and 200B. The purpose of the carbon filter 196 is to retain the swarf within the cartridge 16. As such, the filter 196 need only be capable of removing particles larger than about 100 microns.

Figure 10:
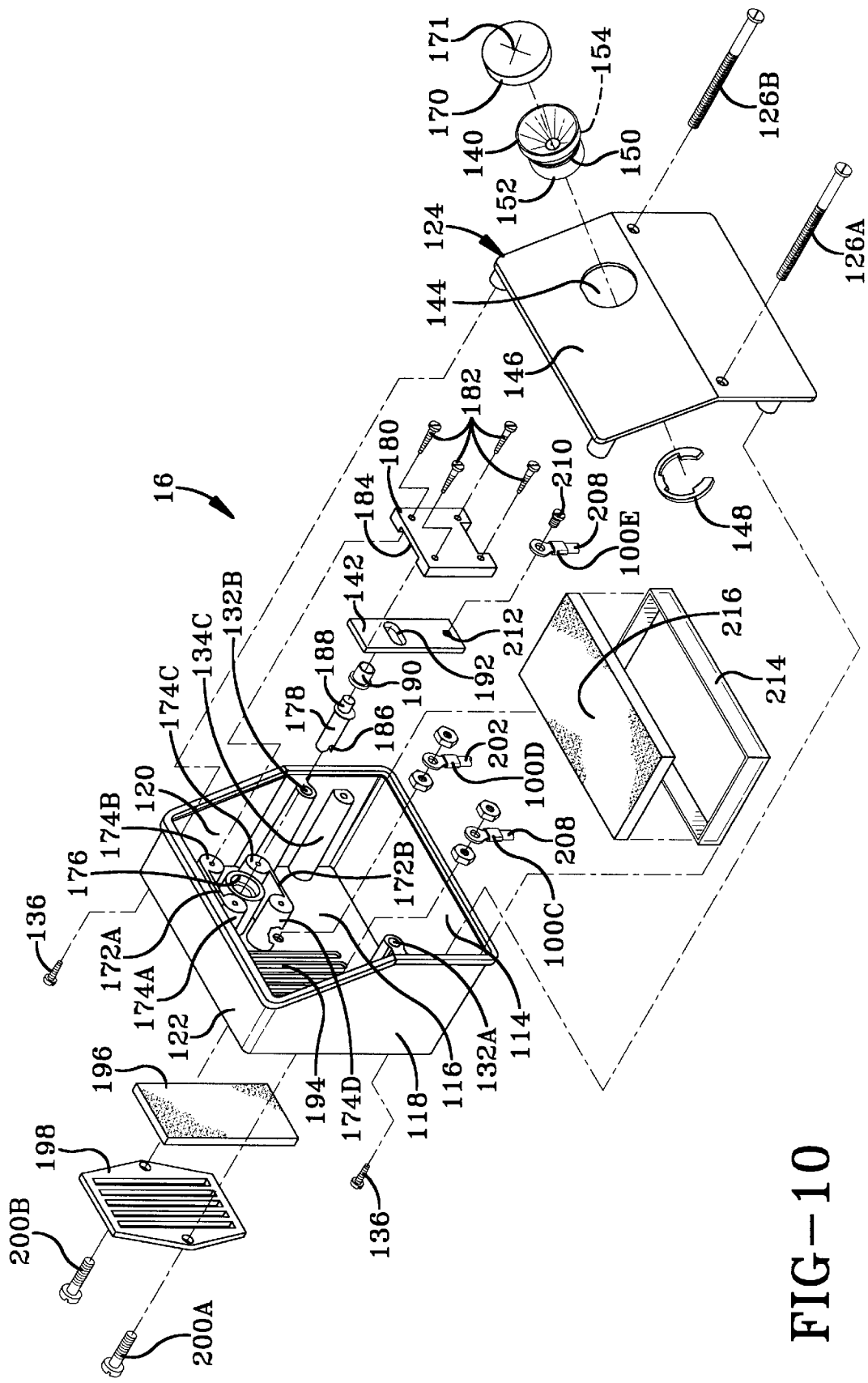
FIG. 10 is an exploded perspective of the cartridge sub-housing.
Figure 11:
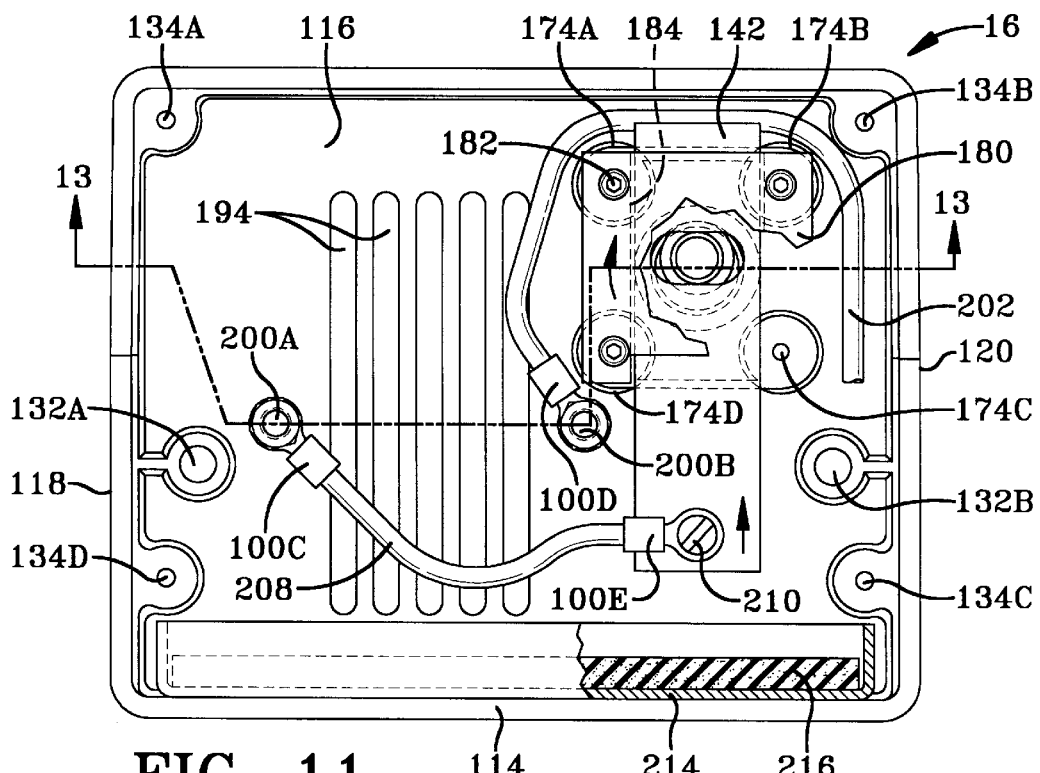
FIG. 11 is an enlarged frontal elevation of the cartridge sub-housing depicting the movable electrode at one end of its linear displacement, the view being partially broken away to reveal not only the mechanism by which the movable electrode is reciprocated but also the means by which to capture any residual liquids.
Figure 12:
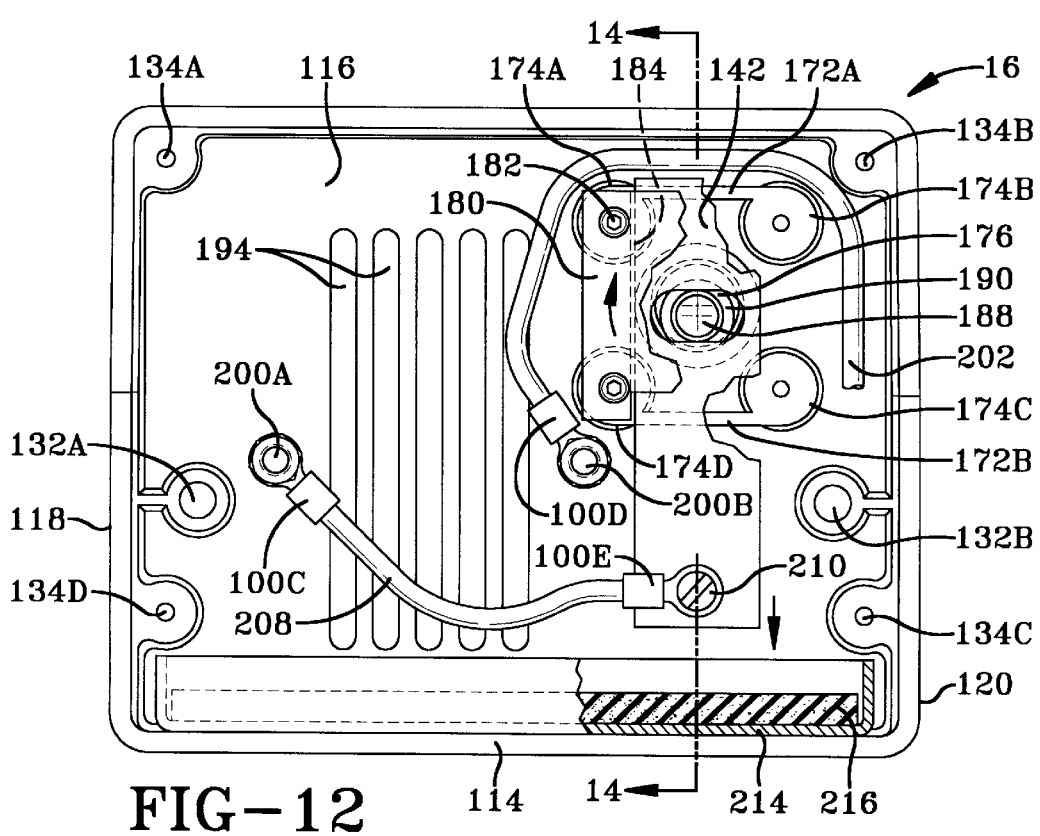
FIG. 12 is a view similar to FIG. 11, but depicting the movable electrode at the opposite end of its linear displacement.
Figure 13:
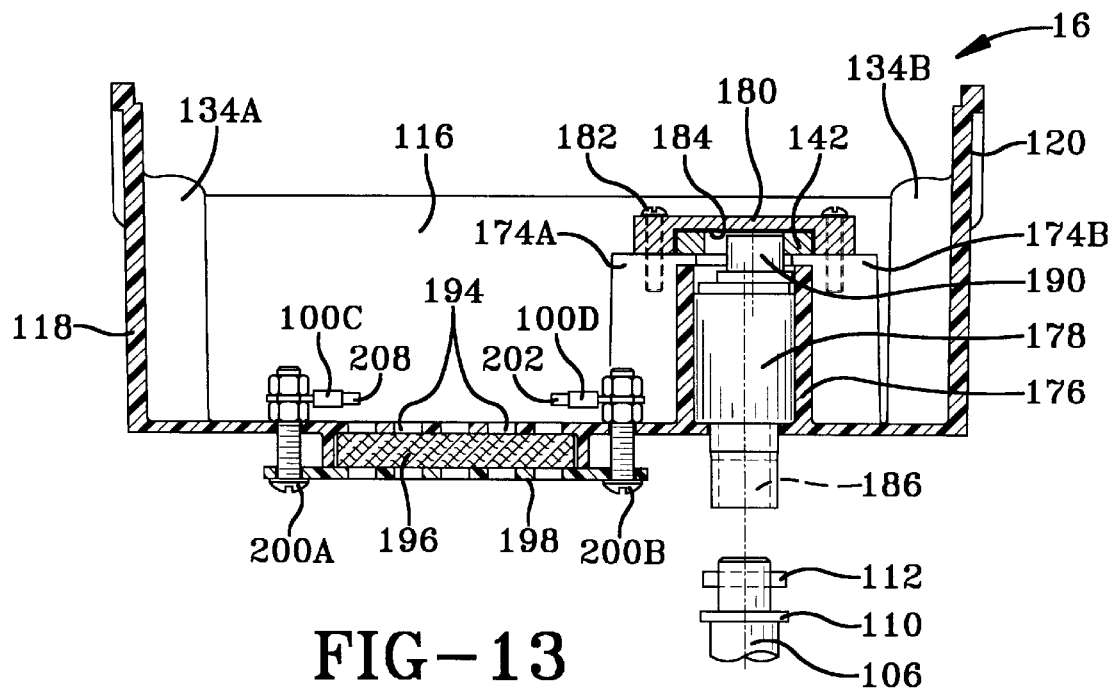
FIG. 13 is a transverse section taken substantially along line 13—13 of FIG. 11.
Figure 14:
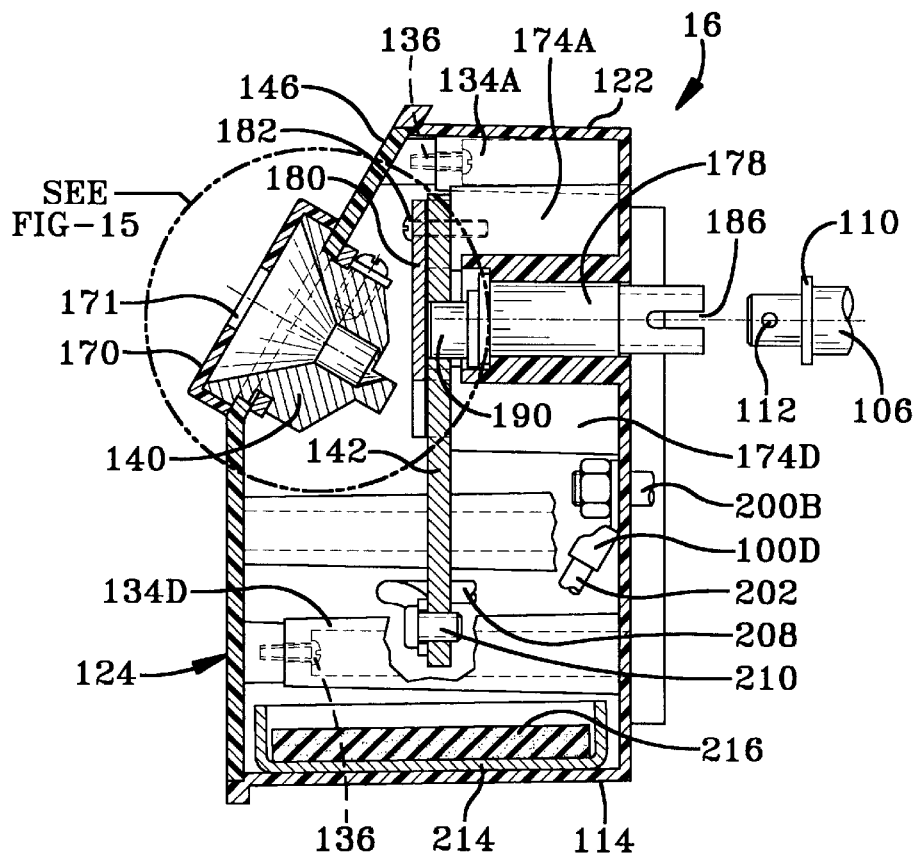
FIG. 14 is a vertical section taken substantially along line 14—14 of FIG. 12.

With continued reference to FIGS. 10 through 12, each nut and bolt combination 200 also mounts an electrical spade connector 100 within the cartridge 16. A wire 202 electrically joins the spade connector 100D with a spade connector 100F that is secured to electrode 140 by the cap screw 204 (FIG. 15) that is receivable within a threaded bore 206 in the body portion 152 of the fixed electrode 140. Similarly, a wire 208 electrically joins the spade connector 100C with a spade connector 100E that is secured to electrode 142 by the cap screw 210 that is receivable within a threaded bore 212 in electrode 142.

When the cartridge 16 is mounted on the primary sub-housing 14, the electrically conductive nut and bolt combinations 200A and 200B, respectively, engage the resilient contact bars 96A and 96B to effect a fast-make coupling and thereby complete the electrical circuit from the spade connectors 100A and 100B conjoined with the contact bars 96A and 96B to the two electrodes 140 and 142.

Also with reference to FIGS. 10 through 12 it can be observed that a metallic tray 214 may be received on the base wall 114 of the cartridge 16. The tray 214 is intended not only to receive the hot swarf as it drops from the movable electrode 142 but also to receive and contain any fluids that might not be vaporized by the heat produced as a result of the arcing of the electrical energy as it passes between the needle N and the electrodes 140 and 142. A heat-resistant sponge 216 may be secured within the tray 214 to absorb any fluids not vaporized and thereby assure their retention within the cartridge 16. A germicidal fluid may be absorbed into the sponge 216 prior to placing the apparatus 10 in service. Although not depicted, a germicidal lamp that is preferably a low wattage, low-pressure mercury arc variety having a radiation output primarily in the ultraviolet wavelengths may be located within the cartridge 16. The most desirable lamp would transmit ultraviolet energy of shorter wavelengths than the bulbs of most mercury lamps in order effectively to serve its germicidal purpose.

Figure 19:
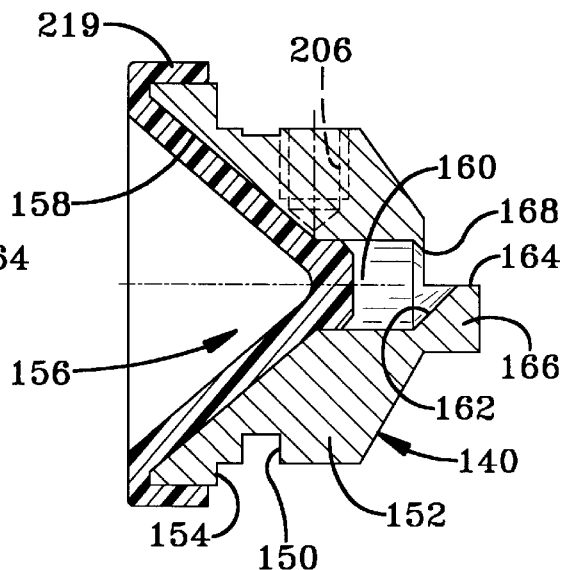
FIG. 19 is cross section taken substantially along line 19—19 of FIG. 16, but depicting a storage plug operatively inserted in the fixed electrode.

It should be appreciated that when the cartridge 16 is removed from the primary sub-housing 14 it is desirable to close the central opening 156 through the fixed electrode 140 of the full cartridge. As depicted in FIG. 19, a plug 219—which conforms to the conical wall 158, and perhaps the cylindrical passage 160 of the central opening 156—may be required to be substituted for the protective cap 170 effectively to seal the fixed electrode 140 after the cartridge 16 has been removed from the primary housing 12. Thus, when one cartridge 16 is filled and needs to be replaced with an empty cartridge 16, a plug 219 may be provided with the replacement cartridge 16. The protective cap 170 can easily be transferred from the full cartridge 16 to the empty cartridge 16, and the fixed electrode 140 on the full cartridge 16 may be closed with a plug 219.

Returning again to FIGS. 1 through 3, the primary sub-housing 14 has a cover 218. The cover 218 has a slanted, frontal surface 220 through which the control read-outs may be presented. For example, three round apertures may receive the light emitting diode (LED) displays 222A, 222B and 222C which, respectively, reflect: (1) that power is available to the apparatus 10; (2) that the apparatus 10 is in the process of effecting an electrical destruction of a needle; and, (3) that the cartridge is full and further usage of the apparatus 10 is precluded until the full cartridge 16 has been replaced with an empty cartridge. A rectilinear aperture may receive a four digit, read-out 224 that may tell, in selected units, the number of needles that have been destroyed by the apparatus 10, the remains of which are currently residing in the cartridge 16.

From the slanted, frontal surface 220, the cover 218 slopes downwardly and rearwardly to join the three-sided, rectilinear skirt 226 which opposingly mates with the side walls 18 and 20 as well as the rear wall 22 of the primary sub-housing 14. That is, the side walls 228 and 230, respectively, opposingly engage the side walls 18 and 20 of the primary sub-housing 14, and the rear wall 232 of the skirt 226 opposingly engages the rear wall 22 of the primary sub-housing 14. That portion of the cover 218 which slopes downwardly and rearwardly to join the skirt 226 comprises: the main upper panel 234—which joins the upper edge of the slanted, frontal surface 220 with the upper edge of the rear wall 232; two, smaller triangular panels 236A and 236B—which join the haunched edges of the slanted frontal surface 220 with the respective intersections of the rear wall 232 with the two side walls 228 and 230; and, the two larger triangular panels 238A and 238B—which conjoin the lateral edges of the slanted, frontal surface 220 with the respective side walls 228 and 230 of the skirt 226 as well as the two smaller triangular panels 230A and 230B. A handle 240 may, if desired, be provided on the main upper panel 234 of the cover 218.

Figure 20:
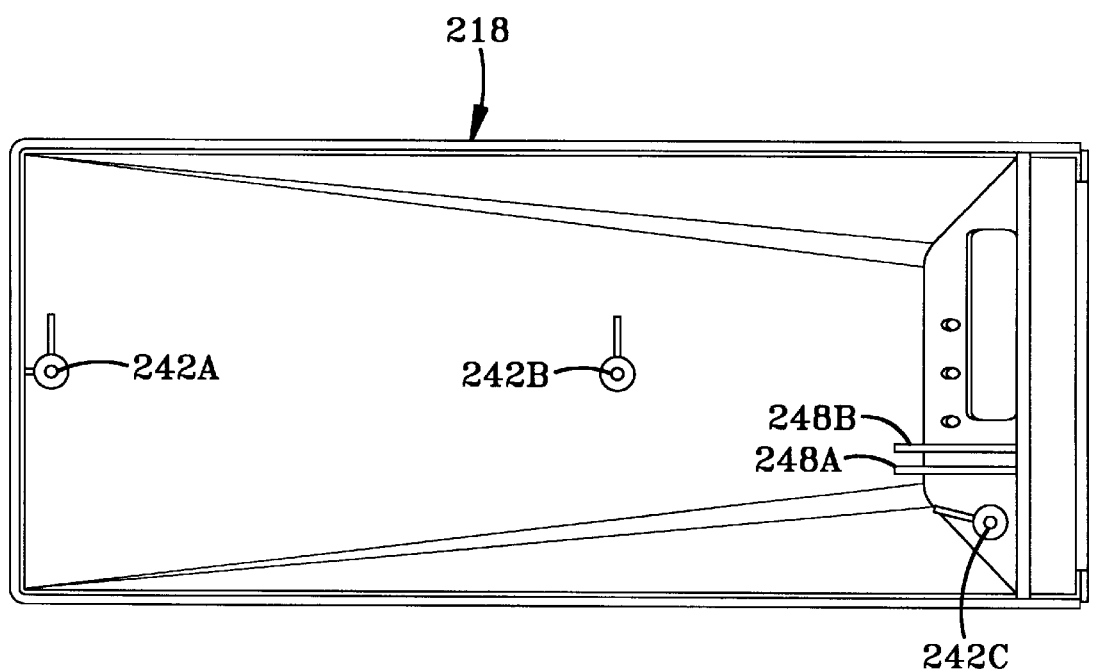
FIG. 20 is a bottom plan view of the cover employed with the primary sub-housing; and, FIG. 21 is a schematic wiring diagram for one mode of the circuitry that may be employed in the present invention.

A plurality of stand-offs 242A, 242B and 242C may be provided on the underside of the cover 218 (FIG. 20) opposingly to engage a like number of stand-offs 244 that extend upwardly from the base 24 of the primary sub-housing 14 (FIGS. 4 and 5). Self-threading screws 246 may extend upwardly within the stand-offs 244 threadably to engage the opposed stand-offs 242 and thereby secure the cover 218 to the primary sub-housing 14. Here, too, disassembly is discouraged by virtue of the fact that the screws 246 can not be accessed unless the environment-protecting filter 32 is first removed.

Interiorly of the cover 218 a pair of laterally spaced, longitudinally oriented blades 248A and 248B extend downwardly to engage, and thus serve to retain, the sleeve bearings 104 received within the bearing supports 102 presented from the mounting block 70.

The present invention, while typically utilizing relatively low DC energy for the control circuits and higher AC energy for the needle destruction as well as for the reciprocation of the movable electrode and the operation of the fan, a person who understands the concepts described herein would be readily capable of operating the apparatus solely with DC voltage, as in the situation where one desired to operate the apparatus 10 from a DC power source in a vehicle. Thus, the particular circuitry of choice will likely depend upon the nature of the environment in which the particular apparatus 10 is to be used.

Figure 21:
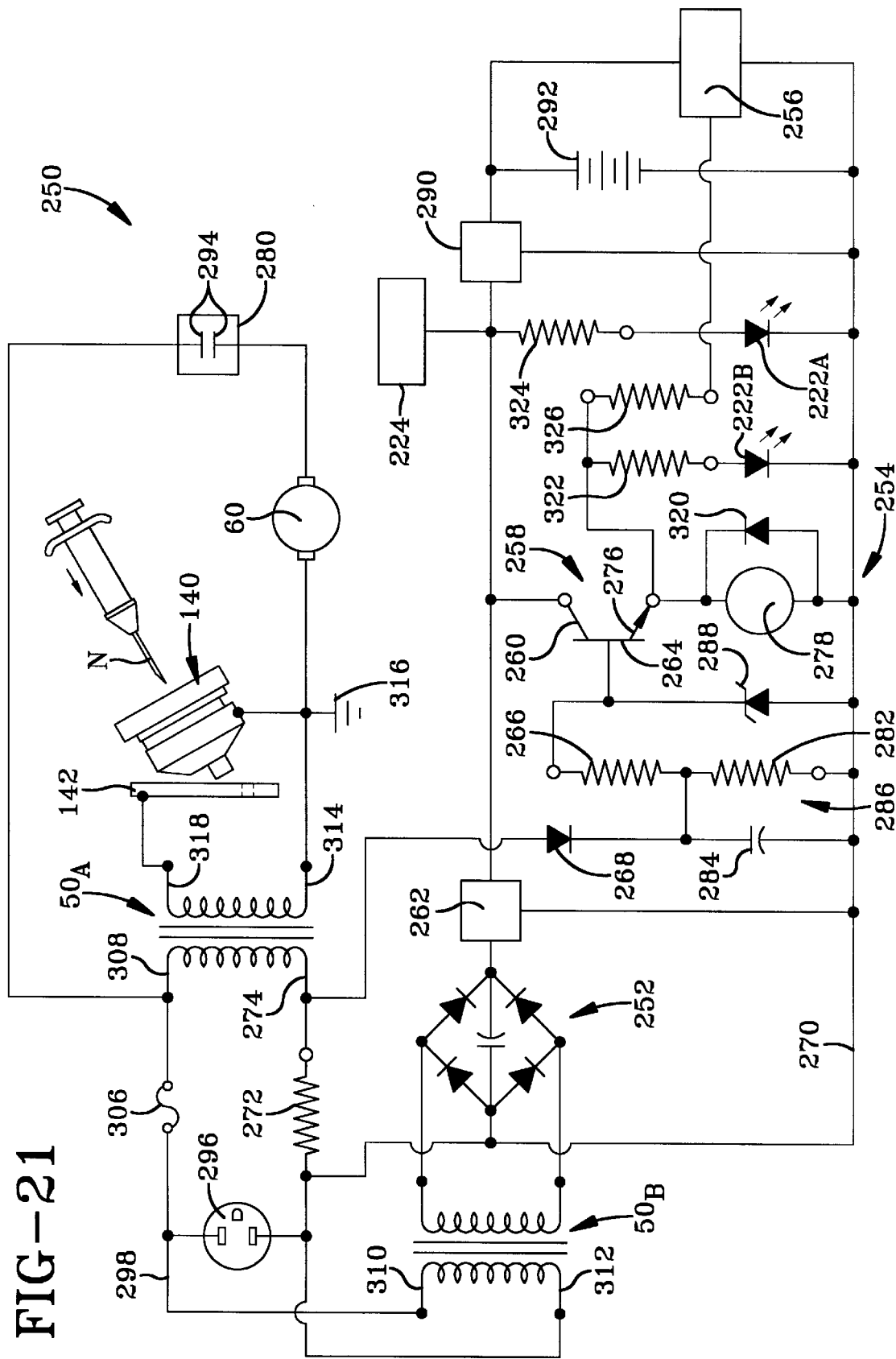

With reference to FIG. 21, representative circuitry 250 for operation from an AC power source is depicted. The circuitry 250 may actually utilize a single, multi-tapped transformer 50, as depicted in the heretofore described structural arrangement of the apparatus 10, but solely for the purpose of clarity the single, multi-tapped transformer 50 will be represented as two transformers $50_A$ and $50_B$. The transformer $50_A$ will supply the high energy output employed to disintegrate the medical instrument, such as a needle, and the transformer $50_B$ will supply the required low energy necessary to operate the control circuitry and the desired logic circuits.

Specifically, the transformer $50_B$ is connected with a conventional, diode bridge rectifier 252 which supplies DC power to a control circuit 254 that furnishes an appropriate count signal to a counter 256. The representative control circuit 254 employs a NPN transistor 258, the collector 260 of which is connected to the rectifier 252 down stream of a voltage regulator 262. The base 264 of the transistor 258 is connected—downstream of a control resistor 266 and a diode 268—to one AC power conductor 270 that feeds the transformer $50_A$. As shown, the connection to the power conductor 270 may be effected between a shunt resistor 272 and one of the AC power-input taps 274 for the transformer $50_A$. The emitter 276 of the transistor 258 is connected to send a signal to the counter 256, and power the coil 278 of a control relay switch 280. The base 264 is also connected to one side of a resistor 282 and capacitor 284 connected in parallel as a standard RC timer circuit 286. In fact, that same side of the RC timer circuit 286 is connected between the control resistor 266 and the diode 268. The other side of the RC timer circuit 286 is connected directly to the power conductor 270. A zener diode 288 is also connected between the base 264 and the power conductor 270.

The control circuit 254 also includes a 5.5 volt regulator 290 and may include a rechargeable 5 volt battery 292 which supply the required voltage to the counter 256, even when the apparatus 10 is not plugged into a power source.

The transistor 258 is configured such that when the base 264 is above the cut-off voltage, the transistor 258 is non-conductive. However, when the base voltage is lowered to or below the cut-off voltage—that is, when the base 264 saturates—the transistor 258 will conduct current from the collector 260 to the emitter 276. The current through the transistor 258 will energize the coil 278 of the control relay switch 280 and thereby close the contacts 294 to complete the circuit through the control relay switch 280.

The AC circuitry 250 is connected to an AC power source by a conventional plug 296 that receives line voltage and transmits that voltage to the transformers $50_A$ and $50_B$ through the AC power conductors 270 and 298, which may be incorporated in a conventional multi-wire cord 300 (FIG. 4) that passes through an aperture 302 in the rear wall 22 of the primary sub-housing 14. A standard strain reliever 304 may be received within the aperture 302 to transfer mechanical stresses applied to the multi-wire cord 300 exteriorly of the sub-housing 14 from adversely affecting the circuitry within the apparatus 10.

The AC power conductor 298 preferably feeds through a fuse 306 and branches to connect: to one side of the control relay switch 280; to the second power-input tap 308 on transformer 50$_A$; and, to a first, power-input tap 310 on transformer 50$_B$. The other AC power conductor 270 connects to the second, power-input tap 312 on transformer 50$_B$. The electric motor 60 connects to the other side of the control relay switch 280 as well as to the first tap 314 on the secondary side of transformer 50$_A$. At this point it can be observed that the first tap 314 is at ground potential, the ground being represented at 316. The fixedly positioned, first electrode 140 is also connected to the first tap 314 on the secondary side of transformer 50$_A$. The fixed electrode 140 may be insulated by making the protective cap 170 from an insulating material. Even so, having that electrode—which is accessible to the user of the apparatus 10—at ground potential is a definite safety feature. The second, linearly reciprocating electrode 142 is connected to the second tap 318 on the secondary side of transformer 50$_A$.

There are certain other features to the circuitry 250 that should be appreciated. For example, a blocking diode 320 spans the coil 278 of the control relay switch 280 to ensure that only current from the emitter 276 would be able to activate the control relay switch 280. A first pull-up resistor 322 in series with the LED 222B also spans the coil 278 of the control relay switch 280 and provides a visual indication that the coil 278 is receiving power and that the device is operating. LED 222A is provided to show that power is on. The LED 222A can, therefore, be electrically interposed between the output of regulator 262 and AC power supply conductor 270. As depicted, a second pull-up resistor 324 is connected in series between the LED 222A and the output of the regulator 262. The third LED 222C is connected to the counter 256 in a manner similar to the connection of the first two LEDs, and it may be wired in a well known manner to provide a visual indication that the counter has reached a predetermined numerical value. The counter 256 may, of course, be connected to a digital read-out 224 that is depicted in the slanted front surface 220 of the cover 218 for the primary sub-housing 14 to allow the user of the apparatus 10 to know, at least generally, how many medical instruments have been destroyed since the receptacle 16 was last replaced. As depicted in FIG. 21, a current limiting resistor 326 may be included in the signal feed line between the emitter 276 of the transistor 258 and the counter 256.

In order to operate the apparatus 10 a needle N is inserted axially through the fixedly positioned first electrode 140 until it comes into contact with the second electrode 142. The metallic needle thus closes an electrical circuit across the two electrodes 140 and 142 which creates an immediate current flow through the secondary winding of transformer 50$_A$. This current flow is reflected through the shunt resistor 272 which triggers an electrical flow through the zener diode 288 and simultaneously charges the RC timer circuit 286. With the zener diode triggered, the base 264 of the transistor 258 saturates, permitting current to flow through the transistor 258. The current flowing through the transistor 258 is reflected in the coil 278 of the control relay switch 280, closing the contacts 294 of the relay switch 280 to start the motor 60 which rotates the fan member 86 and linearly reciprocates the second electrode 142. The current flow through the needle N, and the engagement of the needle against the movable second electrode 142 electrically destroys the needle to the degree that only the metallic swarf remains.

The RC circuit 286 is designed to force the motor 60 to continue to run for a predetermined period of time after the needle has been destroyed. Specifically, the RC timer circuit is designed so that the fan member 86 will continue to rotate for a preselected period of time. As a general rule, that time is selected to permit the fan member 86 to evacuate a volume of air equal to at least two times the volume of the cartridge 16, thereby precluding a reverse flow of potentially toxic air outwardly through the fixed, first electrode 140.

An Alternative Cartridge Sub-housing and Fixed Electrode

Figure 22:
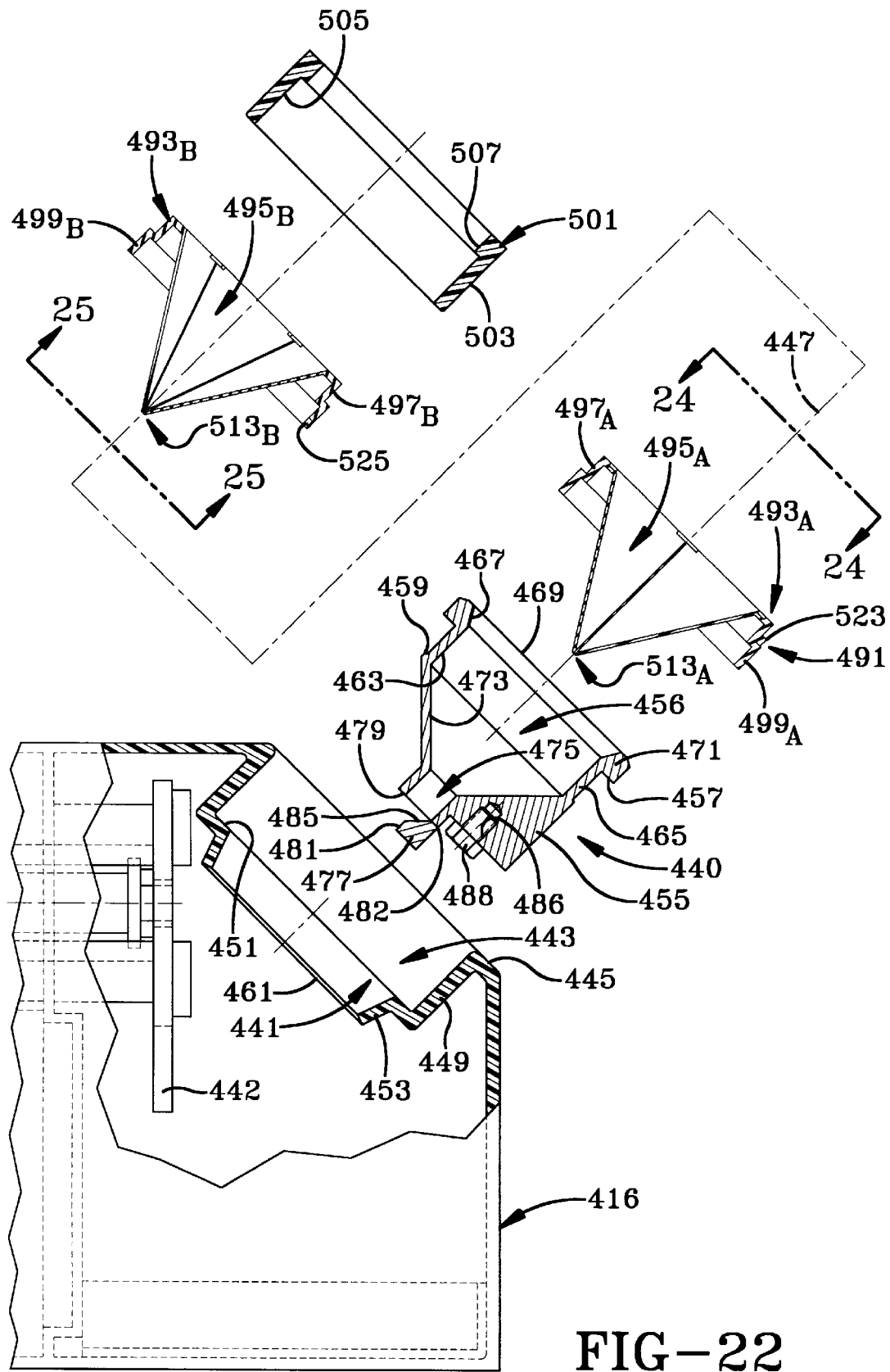
FIG. 22 is a side elevation of a modified cartridge sub-housing, partially broken away, and depicting one alternative form of the fixed electrode assembly in exploded, longitudinal section—the fixed electrode assembly intended to be mounted in said modified cartridge sub-housing.
Figure 23:
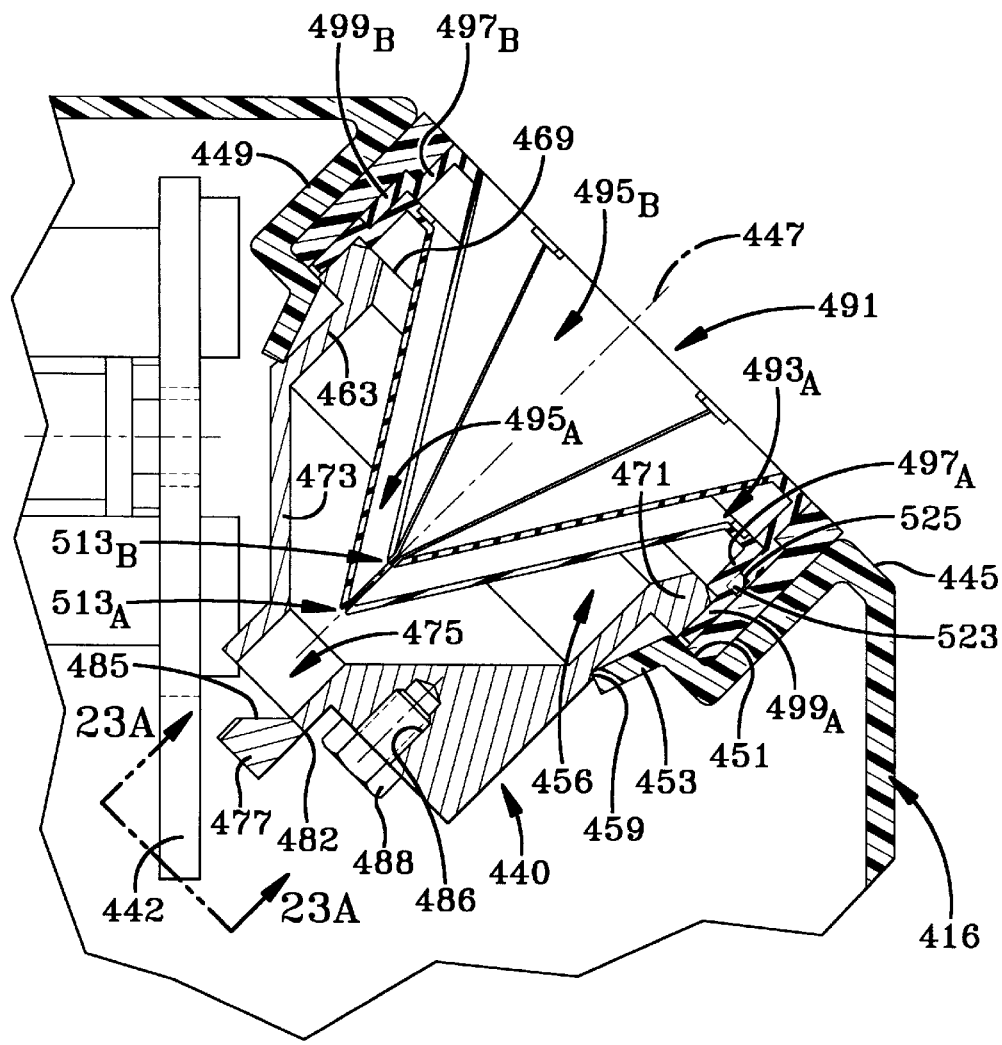
FIG. 23 is a longitudinal section through the alternative fixed electrode assembly depicted in FIG. 22—but not exploded—and with the fixed electrode mounted in the modified cartridge sub-housing.
Figure 29:
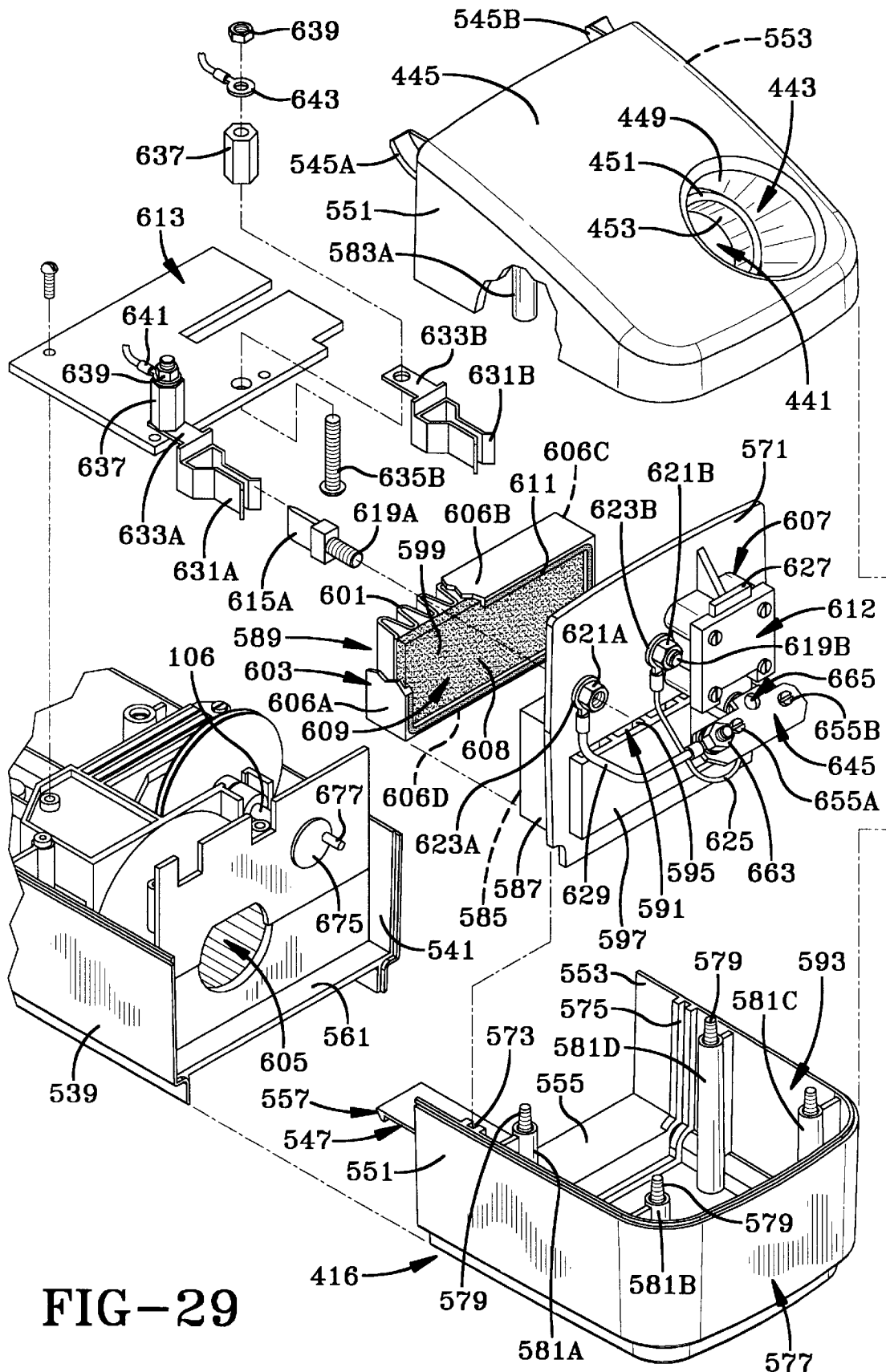
FIG. 29 is an exploded perspective of a further modified cartridge sub-housing.

An alternative form of the fixed electrode utilized in an apparatus of the type to which the present invention is directed—and which is particularly suited to the destruction of medical instruments—is identified generally by the number 440 on FIGS. 22 and 23. The alternative electrode 440 is particularly adapted for use with a cartridge sub-housing 416 having a modified, sloping, frontal portion 445. Specifically, the alternative fixed electrode 440 is mounted to extend partially through an opening 441 at the base of a cup-shaped recess 443 that extends inwardly from the sloping frontal portion 445 of the cartridge sub-housing 416. In the alternative arrangement the axis 447 of the electrode 440 is preferably disposed at approximately 45° with respect to the second, or movable, electrode 442. As shown in FIG. 29, the cup-shaped recess 443 may be laterally offset with respect to the medial portion of the sloping, frontal portion 445.

The cup-shaped recess 443 has an annular wall 449 that extends inwardly from the sloping portion 445 to terminate in an annular seating flange 451 which extends radially inwardly from the inner end of the annular wall 449 and terminates in a truncated, conical latching element 453.

The fixed electrode 440 has a body portion 455 with an annular locating shoulder 457 that defines one face of an annular, outer rim 471 on the fixed electrode 440. The locating shoulder 457 engages the annular seating flange 451 in the cup-shaped recess 443 to define the innermost seating position of the fixed electrode 440 within the cup-shaped recess 443. The body portion 455 presents a locking shoulder 459 that is disposed in opposed, spaced relation to the locating shoulder 457. The axial spacing of the shoulders 457 and 459 is such that when the locating shoulder 457 engages the seating flange 451, the distal edge 461 of the conical locking element 453 will engage the locking shoulder 459 to secure the fixed electrode 440 within the recess 443 provided in the sloping frontal portion 445 of the cartridge sub-housing 416.

The fixed electrode 440 has a central opening 456 defined, in part, by the cylindrical interior surface 463 of the annular wall 465. Axially outwardly of the cylindrical interior surface 463, the central opening 456 has a first conically flared portion 467 which intersects a planar, frontal surface 469 on the annular, outer rim 471 of the fixed electrode 440.

Axially inwardly of the cylindrical inner surface 463 on the annular wall 465, the central opening 456 is defined by a second conical portion 473 that converges axially inwardly to merge into a cylindrical passage 475. A deflection-controlling tip 477 is secured to the inner end surface 479 of the first electrode 440 such that the tip 477 presents a chordal surface 481. It has been determined that operation, and longevity, is enhanced if the deflection-controlling tip 477 is fabricated of a hard material, such as carbide, which may be soldered to the inner end surface 479 of the fixed electrode 440.

The use of a relatively hard deflection-controlling tip 477 in conjunction with the desired inclination of the axis 447 effects a significant horizontal component of the force applied to the medical instrument during insertion, and destruction, thereof within the first electrode 440. The horizontal component of the axial force applied to the medical instrument reacts against the reciprocating second electrode 442 to effect electrical destruction of the medical instrument. At the desired inclination of the fixed electrode relative to the movable electrode this force component results in a consistent electrical contact between the electrodes 440 and 442 through the medical instrument so as to effect efficient destruction thereof. In addition, this geometry significantly enhances the life of the electrode.

Figure 23A:
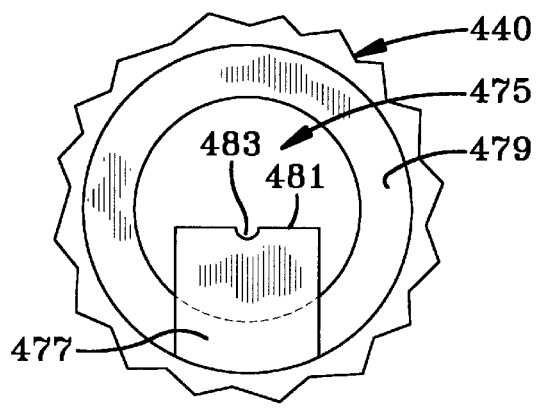
FIG. 23A is an enlarged end elevation of a portion of the fixed electrode assembly taken substantially along line 23A—23A of FIG. 23.

The aforesaid arrangement also tends to preclude separation of the medical instrument from the chordal surface 481 during directional changes in the reciprocation of the second electrode 442, which tends to eliminate undesirable arcing therebetween and thus reduces the wear rate of the fixed electrode 440. What modest arcing may continue to exist, however, will result in the formation of a relatively shallow axial groove 483 (FIG. 23A) in the chordal surface 481. Because the existence of the groove 483 will itself tend to diminish arcing, it may be desired to provide small groove 483 in the manufacture of the deflection-controlling tip 499. In any event, it is deemed that the reduction of arcing occurs not only because the semi-cylindrical configuration of the groove 483 tends to embrace a cylindrical medical instrument, such as a needle—thereby enhancing the surface area contact between the fixed electrode 440 and any surgical instrument in contact therewith—but also because the tip 477 is provided with a planar ramping surface 485 that slopes both radially and axially to intersect the chordal surface 481. It must be appreciated that the cylindrical passage 475, in conjunction with at least the ramping surface 485 on the deflection-controlling tip 477, serve as a guide that directs a medical instrument (such as a needle) inserted through the passage 475 so as to effect an electrical connection between the fixed and movable electrodes 440 and 442, respectively.

Similarly to electrode 140 (FIG. 15), a threaded bore 486 may extend within the electrode 440 parallel to axis 447 thereof in order to receive a cap screw 488 by which to effect an electrical connection to the electrode 440.

An Alternative Protective Cap Assembly

The alternative electrode 440 may also utilize an improved protective cap assembly 491. The protective cap assembly 491 may, as shown in FIGS. 22, 23, 24 and 25, utilize two nested members $493_A$ and $493_B$. The nested members $493_A$ and $493_B$ have respective flexible guard portions $495_A$ and $495_B$ attached to the radially inner, axially outer edge of ring portions $497_A$ and $497_B$. Skirt portions $499_A$ and $499_B$ are, in turn, respectively attached to the radially outer, axially inner extent of each ring portion $497_A$ and $497_B$ in a radially outwardly, offset, disposition. It must be understood that the terminology "attached" is not intended to be limiting; the guard portions 495 as well as the ring portions 497 and the skirt portions 499 of each nested member 493 may well be integrally formed.

In any event, the radially inner ring portion $497_A$ of nested member $493_A$ rests on, and extends axially outwardly from, the planar frontal surface 469 of the rim 471 that extends annularly around the central opening 456 of the fixed electrode 440, as most clearly depicted in FIG. 23. The skirt portion $499_A$ of nested member $493_A$ circumscribes the rim 471 of the fixed electrode 440, and may, as depicted, extend axially inwardly to engage the annular seating flange 451 in the cup-shaped recess 443. The ring portion $497_B$ of nested member $493_B$ rests on, and extends axially outwardly from, the ring portion $497_A$ of the nested member $493_A$. The skirt portion $499_B$ of nested member $493_B$ circumscribes the ring portion $497_A$ of nested member $493_A$. A retention ring 501 has a cylindrical outer surface 503 that engages the interior of the annular wall 449 in the cup-shaped recess 443. The cylindrical inner surface 505 of the retention ring 501 embracingly circumscribes, and thus engages, the both the skirt portion $499_A$ on nested member $493_A$ and the skirt portion $499_B$ on the nested member $493_B$. A radially inwardly directed blocking shoulder 507 on the retention flange 501 engages the radially outer surface of the ring portion $497_B$ on nested member $493_B$ as well as the axially outwardly directed edge on the skirt portion $499_B$ of the nested member $493_B$.

Figure 24:
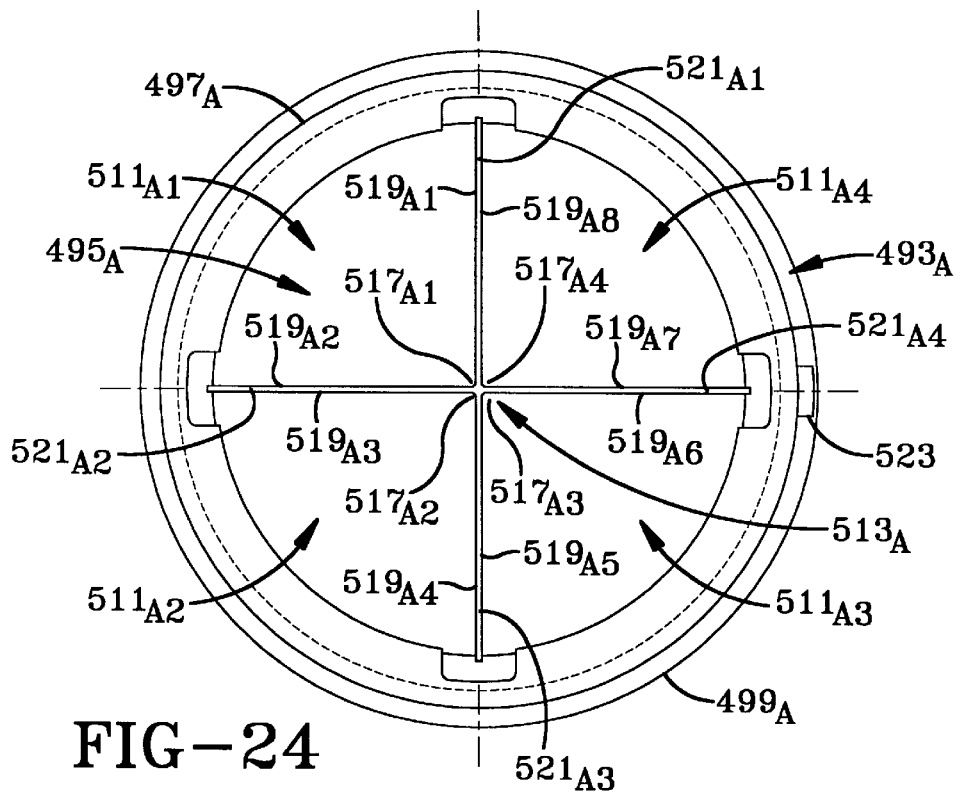
FIG. 24 is an enlarged elevation of one end of an alternative protective cap assembly adapted for use not only with the fixed electrode depicted in FIGS. 22 and 23 but also with the modified cup-shaped recess depicted in FIGS. 26 through 29—FIG. 24 being taken substantially along line 24—24 of FIG. 22.
Figure 25:
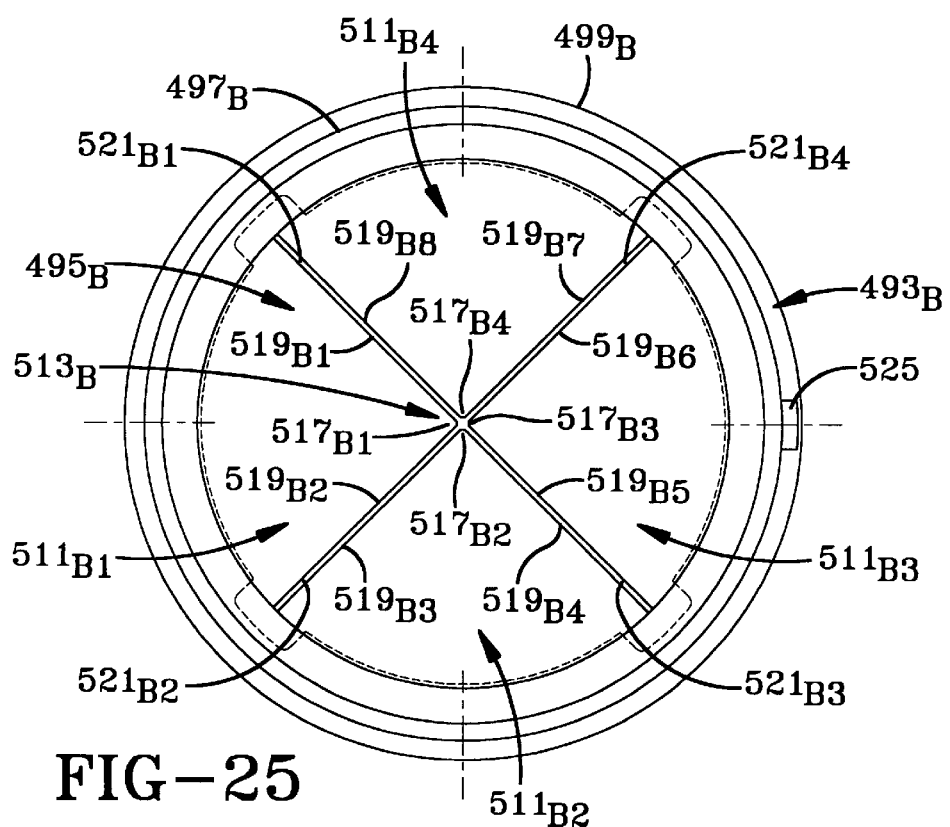
FIG. 25 is an enlarged elevational view taken substantially along line 25—25 of FIG. 22 of that end of the alternative protective cap assembly opposite that end depicted in FIG. 24.
Figure 26:
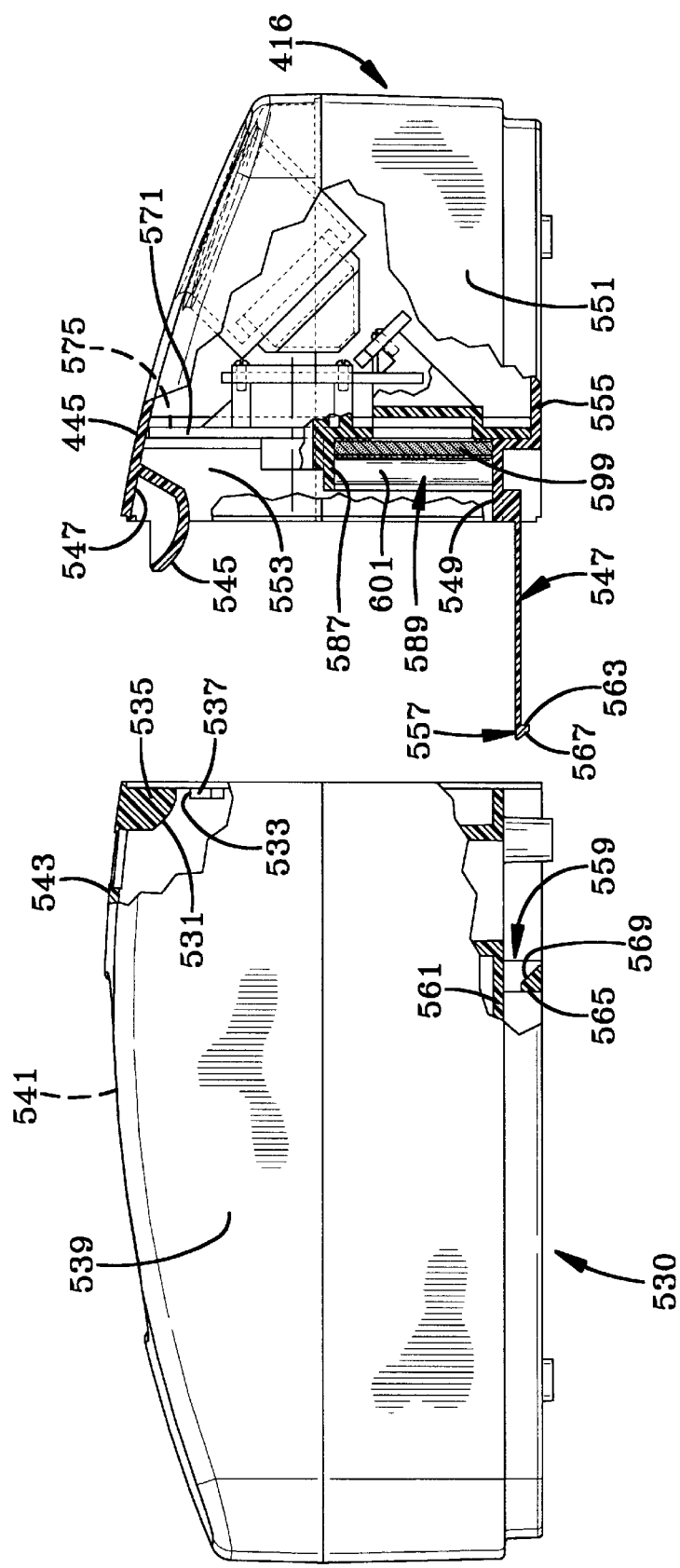
FIG. 26 is a side elevation, partly broken away, of modified primary sub-housing and a modified cartridge sub-housing adapted to be conjoined, but depicted as being longitudinally separated.

As best seen in FIGS. 24 and 25, each guard portion $495_A$ and $495_B$ is preferably comprised of a plurality of cuspids, or conically curved valve flaps, 511 that extend at preferably the same angular inclination to meet at their respective apices $513_A$ and $513_B$. The quad-cuspids 511 forming the closure depicted provides all the functions desired of the guard portions. That is, the cuspids $511_A$ on nested member $493_A$ meet at apex $513_B$. Likewise, the cuspids $511_B$ on nested member $493_B$ meet at apex $513_B$. However, a lesser or a greater number of cuspids 511 might well be employed to achieve the desired results for a given installation.

Each cuspid 511 terminates in a pointed apex 517 that combine to form the consolidated apex 513 of the guard portion and which delineate the downstream extent of each guard portion. The circumferentially successive cuspids 511 have lateral edges 519 that extend to, and form, the individual pointed apices 517. That is, edges $519_{A1}$ and $519_{A2}$ on cuspid $511_{A1}$ meet at apex $517_{A1}$. Similarly, edges $519_{A3}$ and $519_{A4}$ on cuspid $511_{A2}$ meet at apex $517_{A2}$; edges $519_{A5}$ and $519_{A6}$ on cuspid $511_{A3}$ meet at apex $517_{A3}$; and, edges $519_{A7}$ and $519_{A8}$ on cuspid $511_{A4}$ meet at apex $517_{A4}$. The laterally adjacent edges on the successive cuspids are contiguously juxtaposed as represented at $521_{A1}$ through $521_{A4}$ to preclude the reverse flow of swarf through the individual nested members 493. The cuspids $511_B$ on nested member $493_B$ may be similarly configured, as represented at $521_{B1}$ through $521_{B4}$.

As best seen in FIGS. 24 and 25, the nested members 493 are preferably rotated, one with respect to the other, about the axis 447 so that the contiguous juxtaposition of edges, as at $521_A$ on nested member $493_A$ are not aligned with the contiguously juxtaposed edges $521_B$ on nested member $493_B$. Thus, in a quad-cuspid arrangement, the successive guard portions 495 are rotated at 45° with respect to each other. In, for example, a tri-cuspid arrangement the successive guard portions 495 would be rotated at 60° with respect to each other.

To assure the desired relatively rotated disposition of the nested members $493_A$ and $493_B$, a pilot pin 523 may extend axially outwardly from the skirt portion $499_A$ to be received within an appropriate pilot bore 525 on ring portion $497_B$ of nested member $493_B$.

Alternative Connection of Cartridge Sub-housing and Primary Sub-housing

To facilitate mounting and demounting the cartridge sub-housing 416—or the hereinafter further modified cartridge sub-housing 416' depicted in FIGS. 26 through 29—the primary sub-housing 530 is provided with guide surfaces 531 and 533. Guide surfaces 531A and 531B are each arcuately curved about a transverse axis, and as such they define the downwardly and rearwardly directed surface on the respective protuberant bosses 535A and 535B located adjacent the upper wall 543 and extending outwardly in opposed disposition from side walls 539 and 541 of the primary sub-housing 530. Guide surfaces 533A and 533B may comprise the upper edge of ribs 537A and 537B that also extend laterally outwardly from the respective side walls 539 and 541 of the primary sub-housing 530.

Rigid, generally arcuate hinge members 545A and 545B (FIG. 29) located adjacent the side walls 551 and 553 of the further modified cartridge sub-assembly 416' extend downwardly and rearwardly from the underside 547 (FIGS. 26–28) of the sloping front wall 445 at the most rearwardly portion of the further modified cartridge sub-housing 416'. The hinge members 545 engage, and are slidably received between, the spaced guide surfaces 531 and 533. The interaction of each hinge member 545 and the opposed guide surfaces 531 and 533 function as pin-less hinges about which the cartridge sub-housing 416' may be pivoted with respect to the primary sub-housing 530.

A cantilevered latch member 547 is secured to a supporting plate 549 that extends between the side walls 551 and 553 of the modified cartridge sub-housing 416'. The supporting plate 549 is preferably disposed slightly above the level of the base plate 555 of the cartridge sub-housing and in parallel relation to the base plate 555. The latch member 547 is made of a material such as acrylonitrile-butadiene-styrene plastic—commonly referred to as "ABS"—which provides the flexural elasticity required to effect the desired operation of the latch member 547. Of course, it is to be appreciated that practice of the invention is not necessarily limited to ABS, as those skilled in the art can readily select appropriate substitute materials.

The outboard end of the latch member 547 presents a hooked catch 557 that is adapted releasably to engage a locking bridge 559 which is supported from, and extends laterally beneath, the base 561 of the modified primary sub-housing 530. Specifically, the hooked catch presents an inboard, planar face 563 which extends substantially perpendicularly with respect to the latch member 547 in order to engage the planar outboard surface 565 on the locking bridge 559. The hooked catch 557 also presents an inclined outboard face 567 which is adapted to interact with a beveled surface 569 presented from the locking bridge 559.

Figure 27:
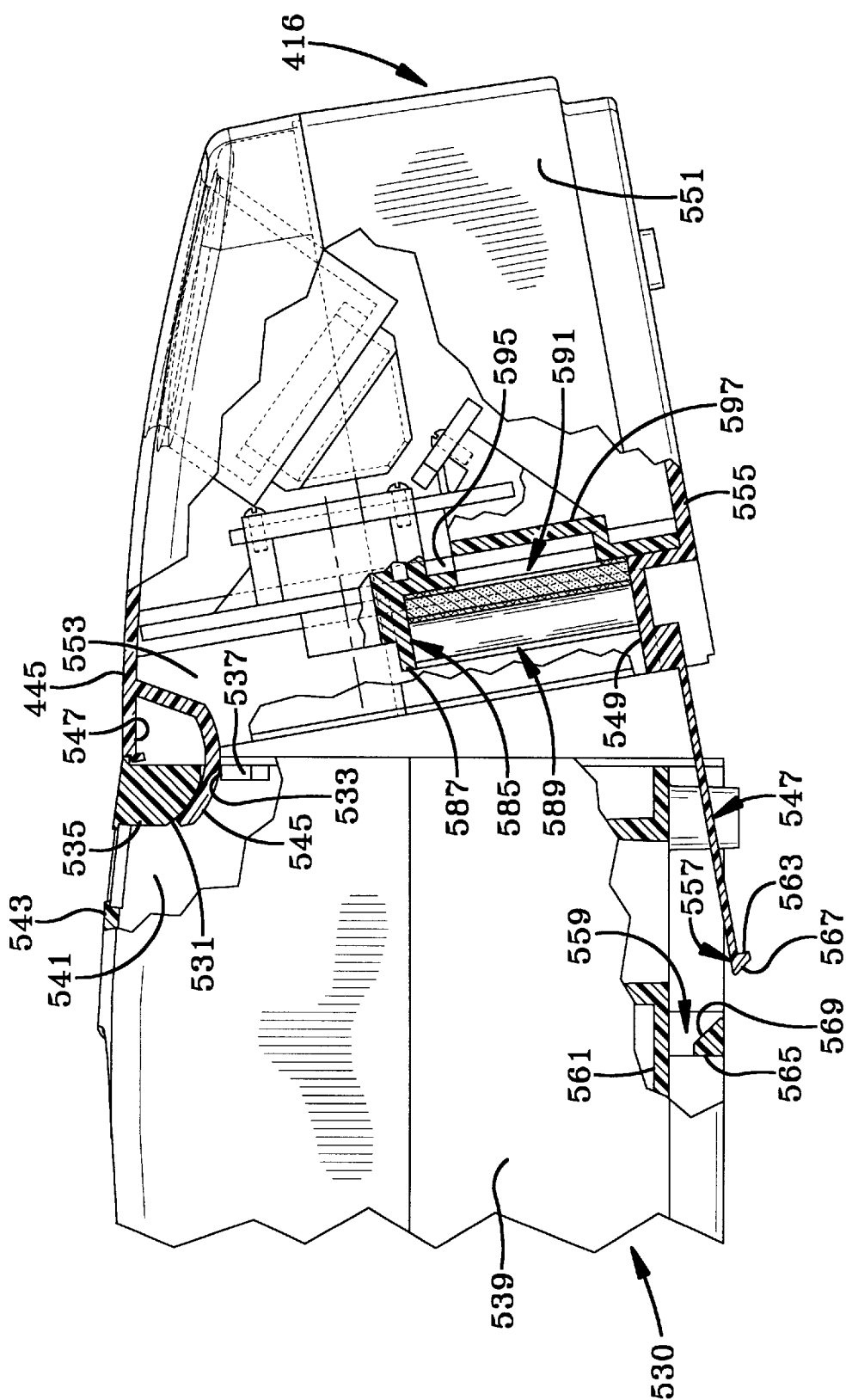
FIG. 27 is an enlarged, partial side elevation, also partly broken away, depicting the modified primary and cartridge sub-housings depicted in FIG. 26, but with the sub-housings partially connected—as would be the situation if said sub-housings were either in the process of either being joined or being separated.
Figure 28:
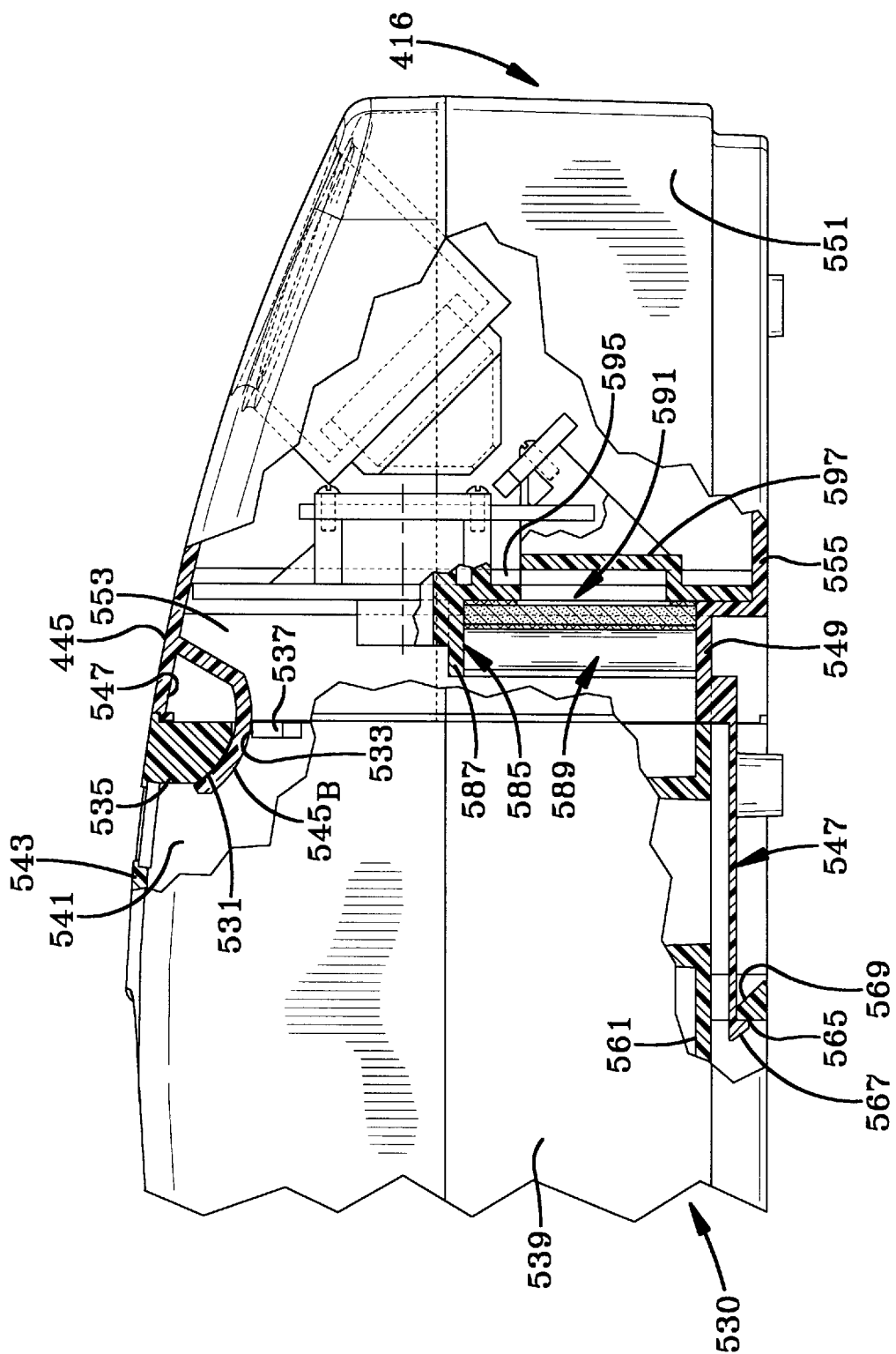
FIG. 28 is an enlarged, partial side elevation, partly broken away, depicting the modified primary sub-housing and the further modified cartridge sub-housing depicted in FIGS. 26 and 27, but with the sub-housings fully joined.

Although some finger pressure may be applied to assure that the inclined face 567 on the hooked catch 557 will engage the beveled surface 569 on the locking bridge 559, swinging the cartridge sub-housing 416' downward about the pin-less hinge arrangements, as represented in FIG. 27, will drive the inclined outboard face 567 on the hooked catch against the beveled surface 569 on the locking bridge 559. Such engagement will cam the hooked catch upwardly and allow the planar inboard surface 563 on the hooked catch 557 to pass over the top of the locking bridge 559 and then, by virtue of the flexural elasticity of the latching member 547, the planar inboard face 563 on the hooked catch 557 will be forced to drop into locking engagement with the planar outboard surface 565 on the locking bridge 559, as shown in FIG. 28. Conversely, it should now be apparent that finger pressure directed upwardly against the cantilevered latch member 547 will raise the hooked catch 557 sufficiently to release the engagement between the planar inboard face 563 on the hooked catch 557 from the planar outboard face 563 on the locking bridge 559 so that the cartridge sub-housing 416' can be swung outwardly and away from the primary sub-housing 530, also as depicted in FIG. 27.

Further Modification to the Cartridge Sub-housing

The cartridge sub-housing 416' may be further modified to include a removable rear wall 571. To facilitate assembly, the rear wall 571 may be supported by opposed slots 573 and 575 provided on the respective side walls 551 and 553 of the modified cartridge sub-housing 416'. Thus, when the sloping portion 445 is secured to the base portion 577 of the cartridge sub-housing 416' the rear wall 571 will be fixedly secured within the modified cartridge sub-housing 416'. In the customary manner hereinbefore described, the sloping portion 445 may be secured to the base portion 579 by self-threading screws 579 which extend upwardly through the stand-offs 581A through 581D presented from the base portion 577 to engage the opposed stand-offs 583 (only 583A is depicted) presented from the under side of the sloping front portion 445.

The rear wall 571 also includes a filter receiving recess 585 defined by a peripheral wall 587. As shown, the filter receiving recess 585 may be rectilinear to receive a filter pack 589. That portion of the rear wall 571 circumscribed by the peripheral wall 587 is provided with a flow passage 591 which communicates between the interior 593 of the cartridge sub-housing 416' and the filter receiving recess 585. As depicted, the flow passage 591 may comprise a plurality of apertures 595 which penetrate an offset portion 597 of the rear wall 571.

The filter pack 589 may, of course, be adapted to the specific use to which the apparatus 10 is to be applied, but for use in the medical field the filter pack 589 may include both a carbon filter 599 and an accordion-folded environmental protection filter 601. As best represented in FIG. 29, the filter pack 589 may be encased in a container 603 such as the rectilinear box-shaped arrangement depicted that may be made of cardboard and then cemented within the filter receiving recess 585. The perimeter walls 606A, 606B, 606C and 606D may define a rectangular outer shape, and the fifth wall 607 is penetrated by an inlet 609 which may be circumscribed by a seal 611 that confines entry from the interior 593 of the cartridge sub-housing 416' to the filter pack 589 only through the flow passage 591. Adjacent the inlet 609 the filter pack 589 employs the carbon filter layer 599 which removes particulate material larger than about 7 to 10 microns in order to retain the swarf within the interior 593 of the cartridge sub-housing 416' and to remove the odors associated with the burning of the material being destroyed by the apparatus 10. As depicted, the sixth side of the container may remain open to permit unfettered flow of filtered air through the filter pack 589 into the fan receiving chamber 605 located within the primary sub-housing, as explained in detail with respect to the description of the primary sub-housing 14 depicted in FIG. 4.

The environmental protection filter 601 is utilized to preclude the emission of aerosols, whether toxic or not, from the interior of the cartridge sub-housing 416'. Depending therefore, on the particular use to which a specific apparatus 10 is to be put, it may be sufficient to employ a high efficiency aerosol particulate filter as the environmental protection filter that is capable of a 99.97% dioctylphalate (DOP) efficiency for removing particulate as small as 0.3 microns (commercially available as a HEPA filter) or it may be required to employ an aerosol particulate filter having a 99.998% DOP efficiency capable of removing particulate as small as 0.1 microns (commercially available as an ULPA filter).

Both the HEPA and the ULPA filters are commercially available, and in the volume bounded by approximately 3⅞ inches in width 1⅞ inches in height and 1½ inches in depth (representative dimensions of the filter container 603), the accordion folding permits the accommodation of a commercially available, environmental protection filter having a filtering surface area of as much as four square feet.

The use of the combined filter pack 559 also obviates the necessity to employ a filter between the fan receiving chamber 605 and the exterior of the primary sub-housing. The alternative is best represented in FIG. 4 wherein a filter 32 is utilized between the fan receiving chamber 44 and the exterior of the apparatus 10.

Figure 30:
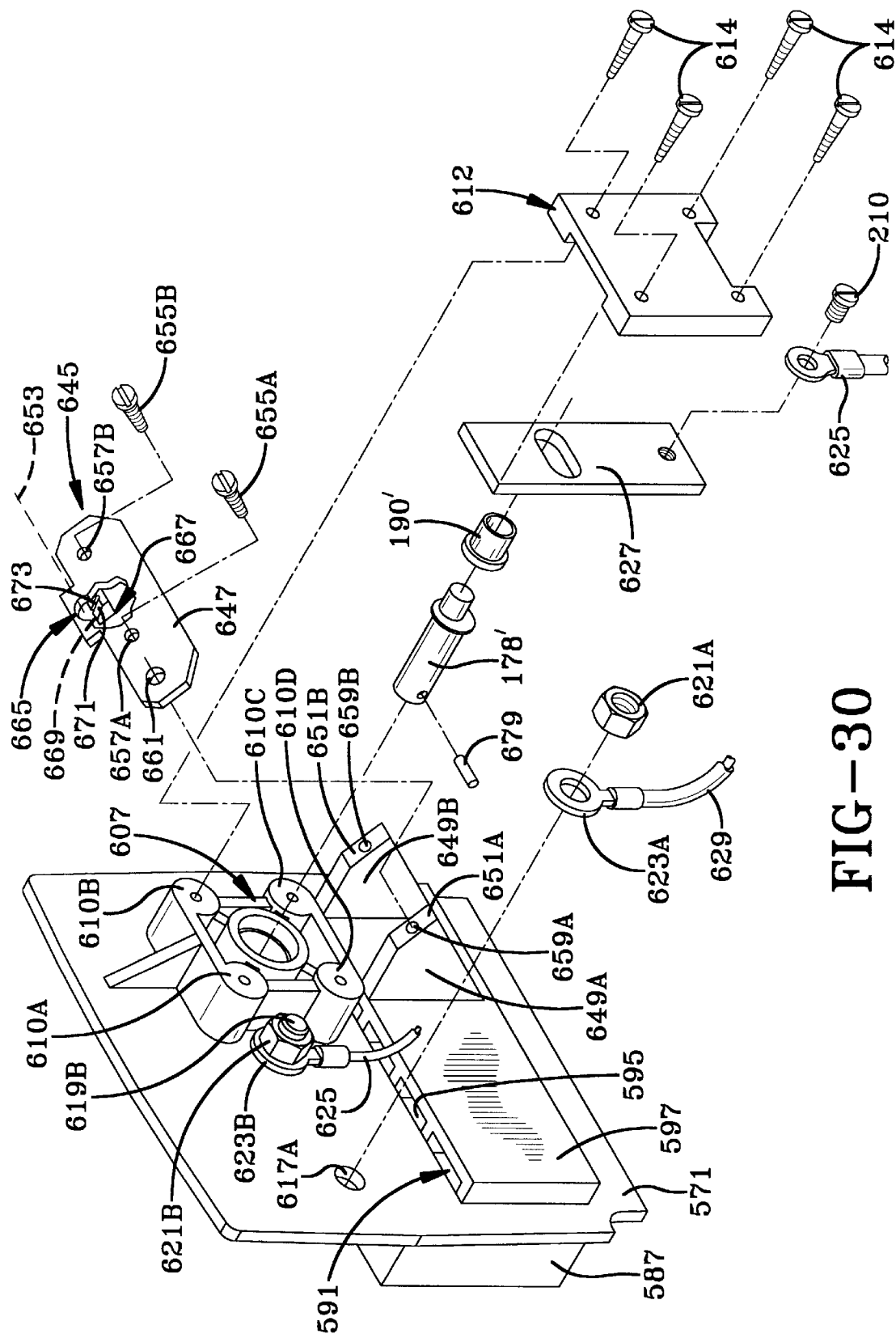
FIG. 30 is an enlarged perspective of the end wall for the further modified cartridge sub-housing depicted in FIG. 29 and depicting, in exploded perspective, the electrodes and other components mounted on said end wall, including a further modification of the fixed electrode.
Figure 31:
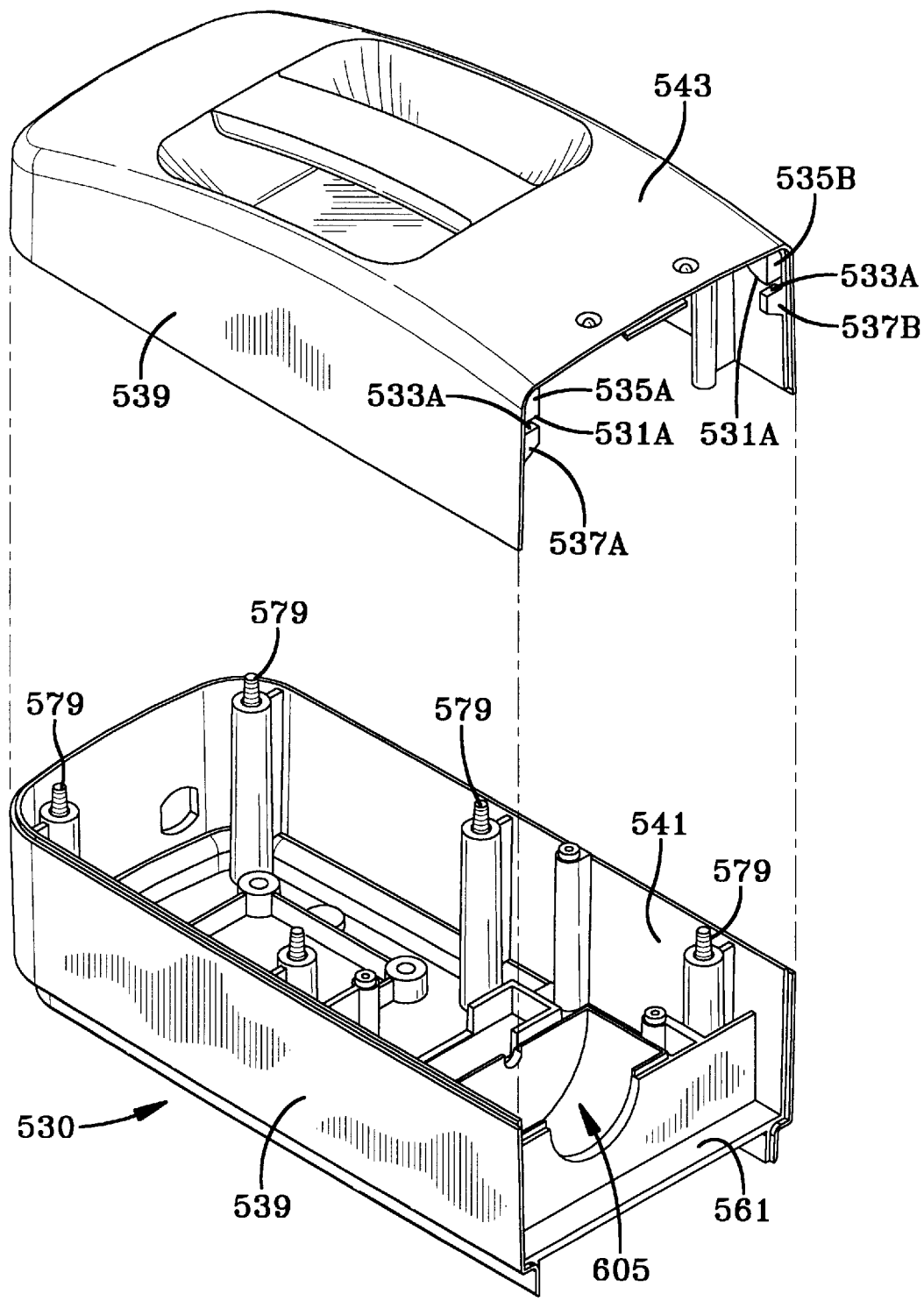
FIG. 31 is an exploded perspective of the primary sub-housing adapted for use with both the modified and the further modified cartridge sub-housings.
Figure 32:
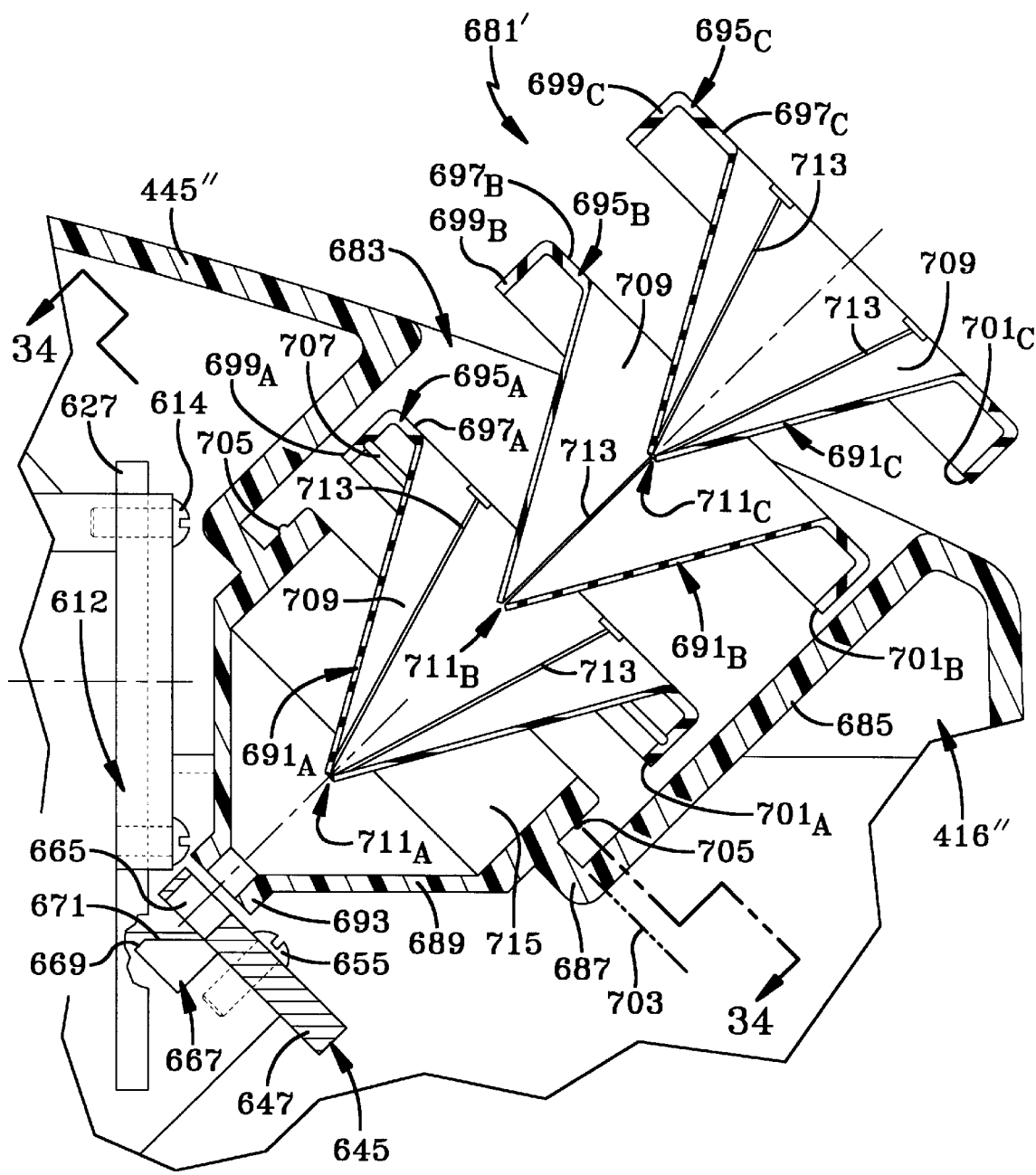
FIG. 32 is a partial, longitudinal section through a still further modified cartridge sub-housing, partially broken away, and depicting yet a further alternative arrangement for a protective cap assembly employed in said cartridge sub-housing.

With continued reference to FIGS. 29 and 30, a mount 607 for the movable electrode 627 may be secured to the rear wall 571 by screws in a manner previously described or, as shown, may be integrally formed with the rear wall 571. In either arrangement the electrode retaining plate 612 may secured to the outboard side of the mount 607, as by a plurality of self-threading screws 614 that extend through the electrode retaining plate 612 to be threadably received within the corner posts 610A through 610D on the mount 607.

A fast-make electrical junction is provided between the primary sub-housing 530 and the cartridge sub-housing 416' so that an electrical connection between the circuit board 613 secured within the primary sub-housing and the electrodes received within the cartridge sub-housing 416' is automatically made, or broken, as the two sub-housing are respectively joined or separated. For example, a pair of blades 615 are mounted through bores 617 in the rear wall 571 of the cartridge sub-housing 416'.

As depicted, the mounting stub 619A which extends axially outwardly from the blade 615A penetrates the bore 617A and may be threaded to receive a nut 621A that performs the dual function of securing the stub 619A to the rear wall 571 and securing a connector 623A on the conductor 625 that is secured to the movable electrode 627 (FIGS. 29 and 30) received on the mount 607 for reciprocation, as previously explained herein in detail with respect to the movable electrode 142 (FIGS. 10 through 14). Similarly, the mounting stub 619B which extends axially outwardly from the blade 615B penetrates the bore 617B and may be threaded to receive a nut 621B that performs the dual function of securing the stub 619B to the rear wall and securing a connector 623B on the conductor 629 that is secured to the fixed electrode 440.

The blades 615A and 615B engage a pair of corresponding spring clips 631A and 631B, respectively, and the spring clips 631 are each provided with an offset mounting flange 633 that are received on a circuit board 613 that is mounted within the primary sub-housing 530. As shown, the mounting bolts 635A and 635B extend upwardly through the circuit board 613 as well as the mounting flanges 633 and pass through spacers 637A and 637B to receive nuts 639A and 391B that serve not only to mount the respective spring clips 631 but also to secure the feed conduits 641 and 643 which provide current for the electrodes 440 and 627 mounted within the cartridge sub-housing 416'.

Further Modified Fixed Electrode

The fixed electrode 440 may be replaced by a modified fixed electrode 645—particularly in those situations where the resiliency of the cartridge sub-housing might induce momentary interruptions of the desired, continuous electrical contact between the medical instrument and the two electrodes during operation of the destruction apparatus 10.

As most clearly represented in FIGS. 29 and 30, the fixed electrode 645 may utilize a base plate 647 that may be secured to rigid, laterally spaced stanchions 649A and 649B that extend outwardly from the rear wall 571, one on either side of the movable electrode 627. The stanchions 649A and 649B present respective receiving surfaces 651A and 651B that are inclined in a common plane to control the angle at which the axis 653 of the fixed electrode 645 is inclined with respect to the movable electrode 627. A pair of, for example, self-threading screws 655A and 655B may pass through bores 657A and 657B in the base plate 647 to be received in bores 659A and 659B recessed into the respective receiving surfaces 651A and 651B in the stanchions 649. A third bore 661 may also be provided in the base plate 647 to assist in effecting a connection between the fixed electrode 645 and the electrical conduit 629. As depicted in FIG. 29, that connection may employ a nut and bolt combination 663.

A cylindrical passage 665 penetrates the base plate 647 to serve as the aperture through which the medical instrument passes to contact the movable electrode 627. A deflection-controlling tip 667 which is also preferably fabricated of a hard material may be soldered to the under surface 669 of the base plate 647. The tip 667 also presents a chordal (relative to the cylindrical passage 665) surface 669 which intersects a planar frontal ramping surface 671. Here, too, a shallow groove 673 that is parallel to the axis 653 may either be provided in the chordal surface 669, or result from any arcing present during usage of the fixed electrode 645. As in the previously described modification of the fixed electrode, the cylindrical passage 665, in conjunction with at least the ramping surface 671 on the deflection-controlling tip 667, serves as a guide that directs a medical instrument (such as a needle) inserted through the passage 475 so as to effect an electrical connection between the fixed and movable electrodes 645 and 727, respectively.

Fast Make Coupling for Movable Electrode

Adoption of the alternative cartridge sub-housing 416' and its facile structural arrangement for achieving the desired demountable connection to the modified primary sub-housing 530 also demands that the mechanical connection between the movable electrode 627 and its drive mechanism be equally facile. The arrangement depicted in FIGS. 4 and 10 utilizes a dog 112 on the electrode drive shaft 106 which interacts with a bifurcation 186 on the opposed end of the transfer shaft 178. With the basic screw connection between the cartridge 16 and the primary sub-housing 14 the dog 112 is readily aligned with the bifurcation 186 during assembly, but with the pin-less hinge arrangement described in conjunction with FIGS. 26 through 28, an even more facile connection is desired. To that end, one may mount a drive disk 675 on the end of the electrode drive shaft 106 and present an eccentric 677 in the nature of a pin that extends axially outwardly of the drive disk 675 from a location that is radially offset from the rotational axis of the electrode drive shaft 106. The eccentric 677 engages a driven pin 679 that extends radially outwardly from the opposed end of the transfer shaft 178'. Such an arrangement provides a virtually flawless mechanism for effecting a fast-make connection between the electrode drive shaft 106 and the transfer shaft 178'—even during the relative swinging movement of the cartridge sub-housing 416' with respect to the primary sub-housing 530 during mounting of the cartridge sub-housing 416' onto the primary sub-housing 530. The remainder of the connection between the transfer shaft 178' and the movable electrode 627 remains unaltered—including the cap screw 210 by which the conductor 625 is secured to the movable electrode 627.

Two Further Variations for a Protective Cap Assembly

When utilizing the fixed electrode 645 that is mounted on the rear wall 571 rather than being received within the cup-shaped recess 443, one may employ a protective cap assembly 681 that is adapted to be received within a simplified cup-shaped recess 683, as depicted in FIGS. 32 through 36.

The cup-shaped recess 683 is also laterally offset with respect to the medial portion of the sloped frontal portion 445" on the cartridge sub-housing 416". The cup-shaped recess 683 has an annular wall portion 685 that extends inwardly from the sloping portion 445" to terminate in an annular seating, and locating, flange 687 which extends radially inwardly from the axially inner end of the annular wall portion 685 and itself terminates in a truncated cone 689 that circumscribes the hereinafter described, nested guard portions 691 of the protective cap assembly 681. The axially innermost extent of the truncated cone 689 defines a barrel, support guide 693 which assures not only that the medical instrument being destroyed enters the cylindrical passage 665 and is guided against the planar frontal surface 671 of the deflection-controlling tip 667 but also serves as a restraining device which absolutely maintains the object being destroyed against the deflection-controlling tip 677 of the fixed electrode 645 as the object being destroyed is fed against the movable electrode 627—irrespective of direction in which the electrode 627 is being moved.

The present protective cap assembly 681 may, for example, utilize three nested members 695. Each nested member 695 has an axially outer ring portion 697 with a flexible guard portion 691 attached to the radially inner edge of the ring portion 697. A skirt portion 699 is attached to the radially outer edge of each ring portion 697.

Figure 33:
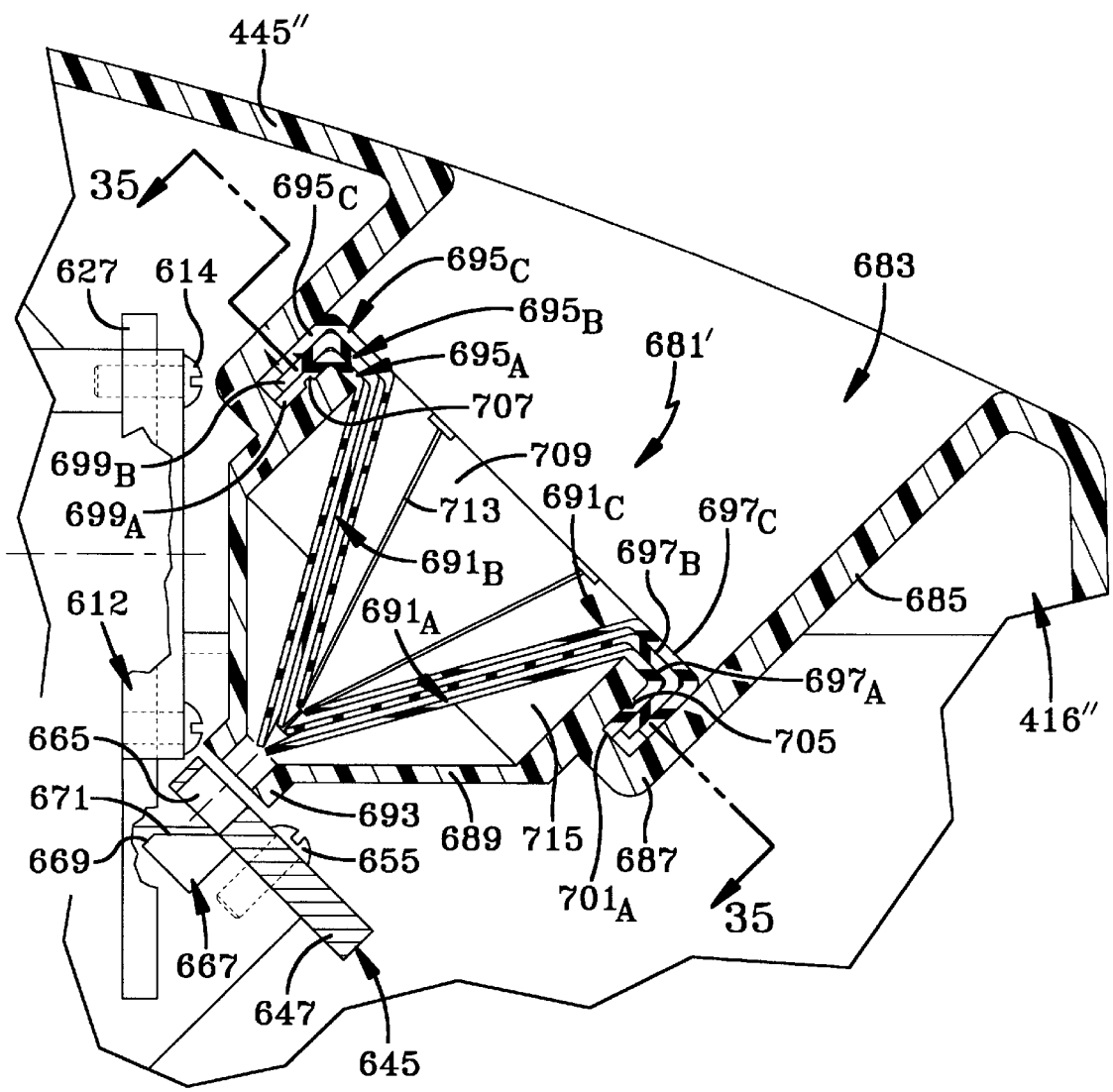
FIG. 33 is a partial, longitudinal section through the still further modified cartridge sub-housing depicted in FIG. 32 but with the further alternative arrangement for the protective cap assembly not exploded.

As best shown in FIG. 33, the ring portions $697_A$, $697_B$ and $697_C$ of the respective nested members $695_A$, $695_B$ and $695_C$ may be contiguously juxtaposed. When so assembled, the skirt portions $699_A$, $699_B$ and $699_C$ may also be concentrically juxtaposed, and each skirt portion 699 may be of an axial dimension such that the respective axially inner edges $701_A$, $701_B$ and $701_C$ terminate in a common transverse plane (not shown) so as simultaneously to engage the seating and locating flange 687 and thereby locate the innermost extent to which the protective cap assembly 681 can be inserted within the cup-shaped recess 683. In any event, it is only really necessary for the axial inner edge 701 of just one skirt portion 699 to engage the seating and locating flange. Thus, edge $701_A$ is typically so chosen, as depicted.

Although one may rely on friction to retain the protective cap assembly 681 within the cup-shaped recess 683, it may be desired to provide a means physically to retain the protective cap assembly 681 within the recess 683. One may, of course, rely on the frictional contact between the skirt portions 699 and the concentric walls of the recess 683 which lie adjacent the radially innermost and radially outermost skirt portions $699_A$ and $699_C$, respectively. Conversely, one may rely on one of the adhesives, well known to the rubber and plastic industry. To provide facile removability to the protective cap assembly 681 and yet have an assured retention device, one may provide a retaining flange 705 which extends circumferentially around, and radially outwardly from, the concentric inner, annular wall 715 of the cup-shaped recess 683 to be received within a detent notch 707 that is incised circumferentially within the annually inner surface of the radially innermost skirt $699_A$.

As in the previously described protective cap assembly 491, each nested member 695 of the protective cap assembly 681 may also employ a plurality of cuspids—or conically curved, valve flaps—709 that extend conically to meet at their respective apices 711. Similarly, the circumferentially successive cuspids 709 have laterally adjacent edges 713 that are contiguously juxtaposed to preclude the reverse flow of sparks, swarf, odors or other detritus through the nested members 695. Moreover, the nested members 695 are preferably disposed such that the contiguously juxtaposed edges 713 on one nested member 695 do not align with the contiguously juxtaposed edges 713 on the adjacent nested members 695. As such, nested members $695_A$ and $695_C$ may have their lateral edges 713 aligned, so long as the lateral edges 713 on nested member $695_B$ is offset from the lateral edges on both nested members $695_A$ and $695_C$.

Typically, the nested members may be secured to each other, as by applying an adhesive between the contiguous skirts 699 and/or the contiguous ring portions 697, but one may, of course, utilize pilot pins and pilot bores, if desired, and as previously explained herein with respect to the configuration depicted in FIGS. 22 through 25.

It should be appreciated that some of the materials suitable for making the skirt portions 699 of the protective cap assembly 681 might not have the necessary resilience readily to permit the deformation and recovery of the skirt portions 699 required to assure insertion the skirt portion 699 between the annular wall portion 685 and the concentric, inner annular wall 715 of the cup-shaped recess 683 with its projecting retaining flange 705. In that regard it must be appreciated that the skirt portion 699 must accommodate sufficient distortion for the retaining flange 705 to move along the outer surface of the skirt portion $699_A$ until the flange 705 enters the detent notch 707. Depending, therefore, upon the material from which the skirt portions 699 are fabricated, it may be desirable, or necessary, to provide either circumferentially modified retaining flanges 705 and/or circumferentially modified skirt portions 699 of appropriate radial thicknesses to accommodate insertion of the skirt portions 699 between the radially opposed, and fixed, inner annular wall 715, with the projecting retaining flange 705, and the concentric annular wall portion 685 of the cup-shaped recess 683.

Figure 34:
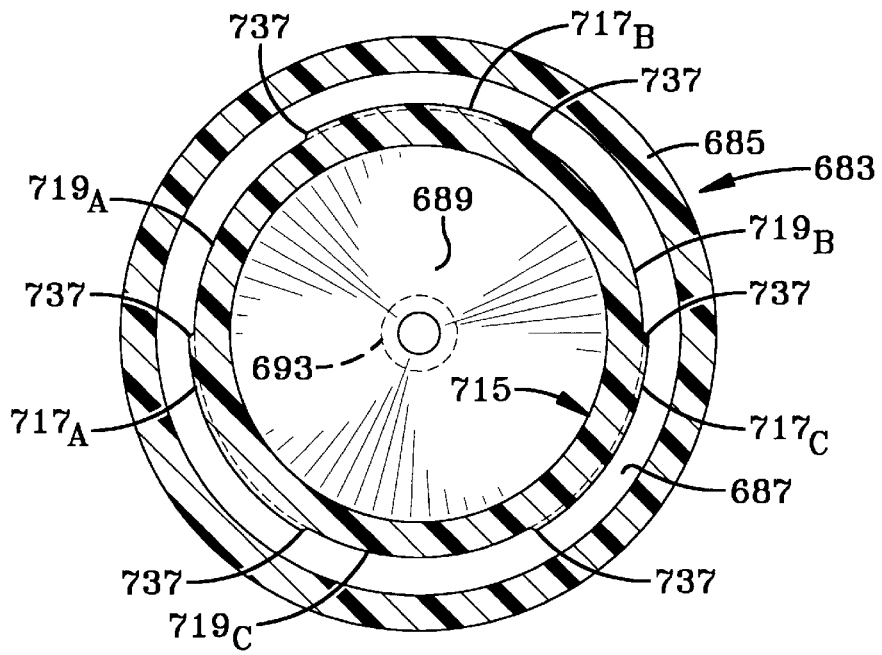
FIG. 34 is an enlarged cross sectional view taken substantially along line 34—34 of FIG. 32.
Figure 36:
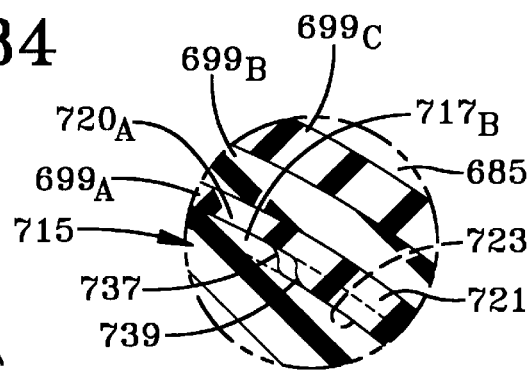
FIG. 36 is a further enlarged cross section of that portion of FIG. 35 defined by the circle superimposed on FIG. 35 and designated SEE FIG. 36.
Figure 35:
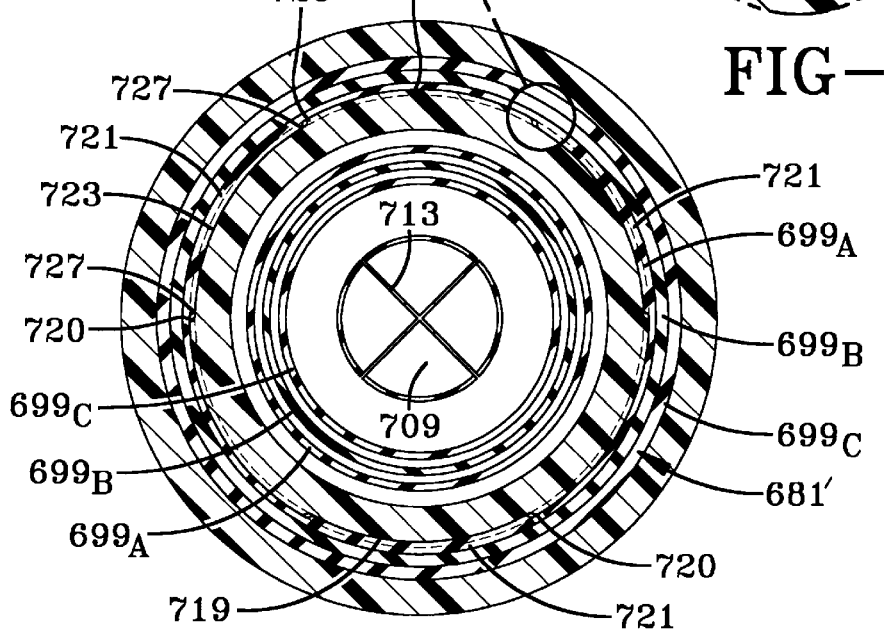
FIG. 35 is an enlarged cross sectional view taken substantially along line 35—35 of FIG. 33.
Figure 37:
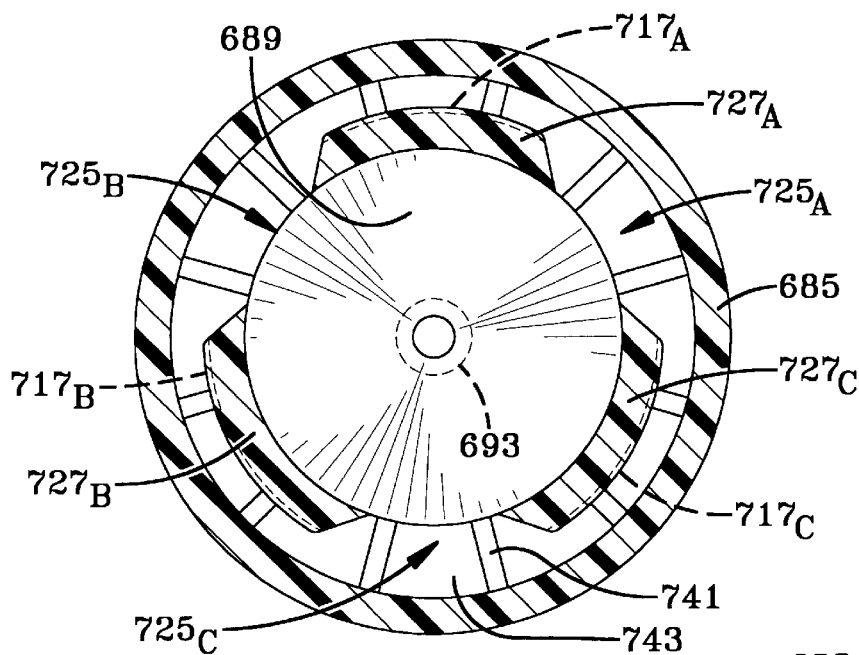
FIG. 37 is a view similar to FIG. 34 but depicting a further variation thereof.
Figure 39:
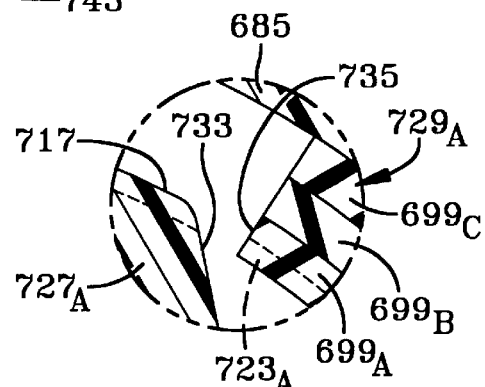
FIG. 39 is a view similar to FIG. 36 but defined by the circle superimposed on FIG. 38 as SEE FIG. 39.

For example, the retaining flange segment 717 on the inner wall 715 may be circumferentially discontinuous to present a plurality of arcuate retaining flange segments 717 which extend radially outwardly of the wall 715, as best shown in FIGS. 34 through 36. Although the number of segments employed is not critical, should one elect to employ three arcuate retaining flange segments 717, each segment 717 could subtend an angle of approximately 60°—in which case the retaining flange segments 717 would be circumferentially spaced at subtended angles of approximately 60°—thus providing three arcuate retaining flange segments $717_A$, $717_B$ and $717_C$ that are circumferentially spaced by three wall segments $719_A$, $719_B$ and $719_C$ that are thinner by an amount equal to the radial projection of the retaining flange segments 717. Alternatively, the inner wall 715 may, as represented in FIGS. 37 through 39, be crenelated to present a gap 725 between successive, circumferentially spaced, crenelated, arcuate wall segments 727 from which the retaining flange segments 717 project, as depicted in FIGS. 37 through 39.

Returning to the embodiment represented in FIGS. 34 through 36, the skirt portion $699_A$ of the protective cap assembly 681' would be modified in conformity with the radially outer surface of the wall 715. That is, the skirt portion $699_A$ would have a plurality of thinner skirt segments 720 and a plurality of thicker skirt segments 721. The thicker skirt segments 721 would include the detent notches 723, and, in fact, the differential thickness between the thinner and the thicker skirt segments 720 and 721, respectively, would need only to be that additional thickness required to provide the detent notches 723 of sufficient depth to receive the retaining flange segments 717. Obviously, therefore, the plurality of thinner and thicker skirt segments would preferably conform to the number and circumferential spacing of the retaining flange segments 717. As such, there would, in the embodiment depicted, be three thinner skirt segments $720_A$, $720_B$ and $720_C$ separated at 60° by the three thicker skirt segments $721_A$, $721_B$ and $721_C$ which are incised to provide the respective detent notches $723_A$, $723_B$ and $723_C$. Insertion of the protective cap assembly 681', therefore, would be accomplished by aligning the radially thinner skirt segments 720 with the retaining flange segments 717 and then axially inserting the protective cap assembly 681' such that the retaining flange segments 717 would slide axially along the radially thinner skirt segments 720 until the detent notches 723 in the thicker skirt segments 721 align with the transverse plane of the retaining flange segments 717 on the inner wall 715. This condition exists when the axially inner edge $701_A$ of the skirt portion $699_A$ engages the seating and locating flange 687. After being thus axially inserted, the protective cap assembly 681' is rotated about its own axis to place each arcuate retaining flange segment 717 within the detent notch 723 incised into the thicker skirt segments 721 of the skirt portion $699_A$.

Figure 38:
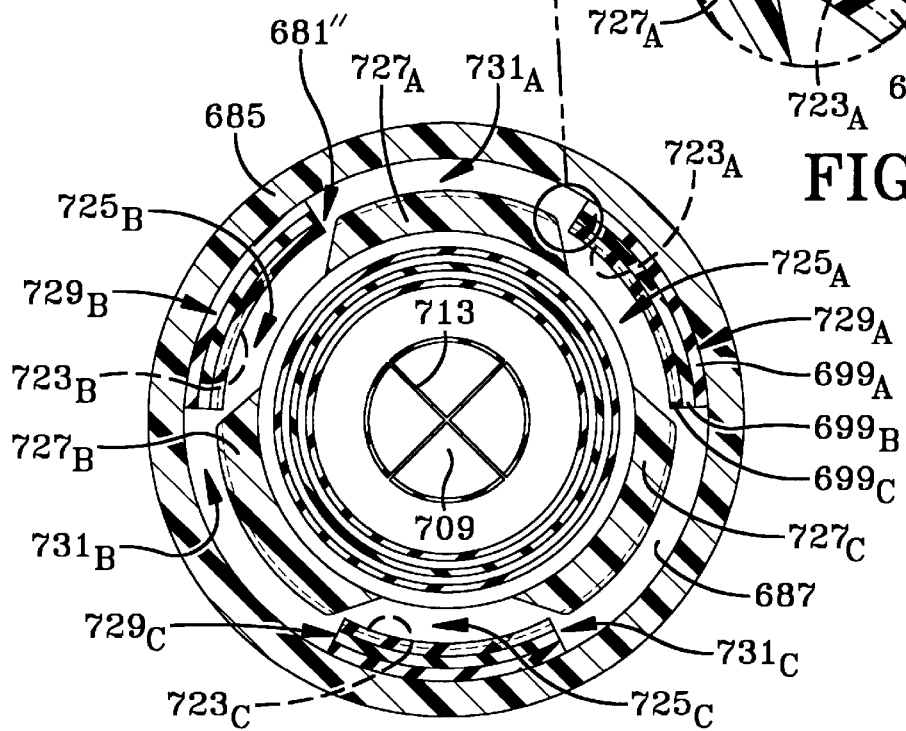
FIG. 38 is a view similar to FIG. 35 but depicting the variation depicted in FIG. 37.

Similarly, the overlapping skirt portions of the nested members in a protective cap assembly 681" may be circumferentially discontinuous, as represented in FIG. 38, such that each skirt flap 729 includes discrete segments of the overlapping skirt portions $699_A$ through $699_C$. Hence, three distinct skirt flaps $729_A$, $729_B$ and $729_C$ would be provided, and each skirt flap 729 could subtend an angle of 60°. For symmetry, the three skirt flaps 729 could be circumferentially spaced at 60° by intervening discontinuity voids $731_A$, $731_B$ and $731_C$. Insertion of the protective cap assembly 681" would be accomplished by aligning the skirt flaps $729_A$, $729_B$ and $729_C$ with the corresponding gaps $725_A$, $725_B$ and $725_C$ between the crenelated wall segments $727_A$ through $727_C$ and then axially inserting the protective cap assembly 681" such that skirt flaps $729_A$ through $729_C$ would slide axially within the corresponding gaps 725 unimpeded until the detent notches 733 on each skirt flap 729 are aligned with transverse plane of the retaining flanges 717 on the corresponding crenelated wall segments 727. As described in the previous paragraph, this condition exists when the axially inner edge 735 of the skirt flaps $729_A$ of skirt portion $699_A$ engages the seating and locating flange 687. At that time the protective cap assembly 681" may be rotated about its own axis to place each skirt flap 729 between the annular wall portion 685 and the appropriate crenelated wall segment 727. Such rotation inserts the retaining flange segments 717 within the appropriate detent notches 723.

In effect, the protective cap assemblies 681' and 681" described in the foregoing paragraphs are retained in their operative location by a type of bayonet connection.

As best shown in FIG. 39, in order to facilitate rotation of the skirt flaps 729 between the annular wall portion 685 and the crenelated wall segments 727 so that the retaining flanges 717 extending radially outwardly from each crenelated wall segment 727 may be readily received within the detent notches 723 in the respective skirt flaps 729, it may be desirable to bevel the axially extending edges of at least crenelated wall segments 727, as depicted at 733, and perhaps even bevel the axially extending edge 735 on at least the radially innermost skirt portion $699_A$ of skirt flaps 729. Because bevelling edge 735 does not appear to be necessary, it is not depicted on the drawings.

Likewise, with reference to FIG. 36, rotation of the protective cap assembly 681' may be facilitated by applying a bevel 737 on the ends of at least the arcuate retaining flange segments 717, and perhaps even bevel the axially extending edge 739 of the thicker skirt segment 721. Here, too, however, the bevelled edge 739 may not be necessary.

To facilitate the formation of the retaining flanges 705 and/or 717, it may be desirable to construct the seating and locating flange 687 as a series of radially extending ribs 741 (FIGS. 34 and 37) rather than as a solid planar member represented in the other figures. This arrangement provides an open sector 743 between the successive, circurferentially spaced ribs 741 through which a forming device (not shown) may be extended during molding of the modified cup-shaped recess 683.

Alternative Electrical Circuitry

Figure 40:
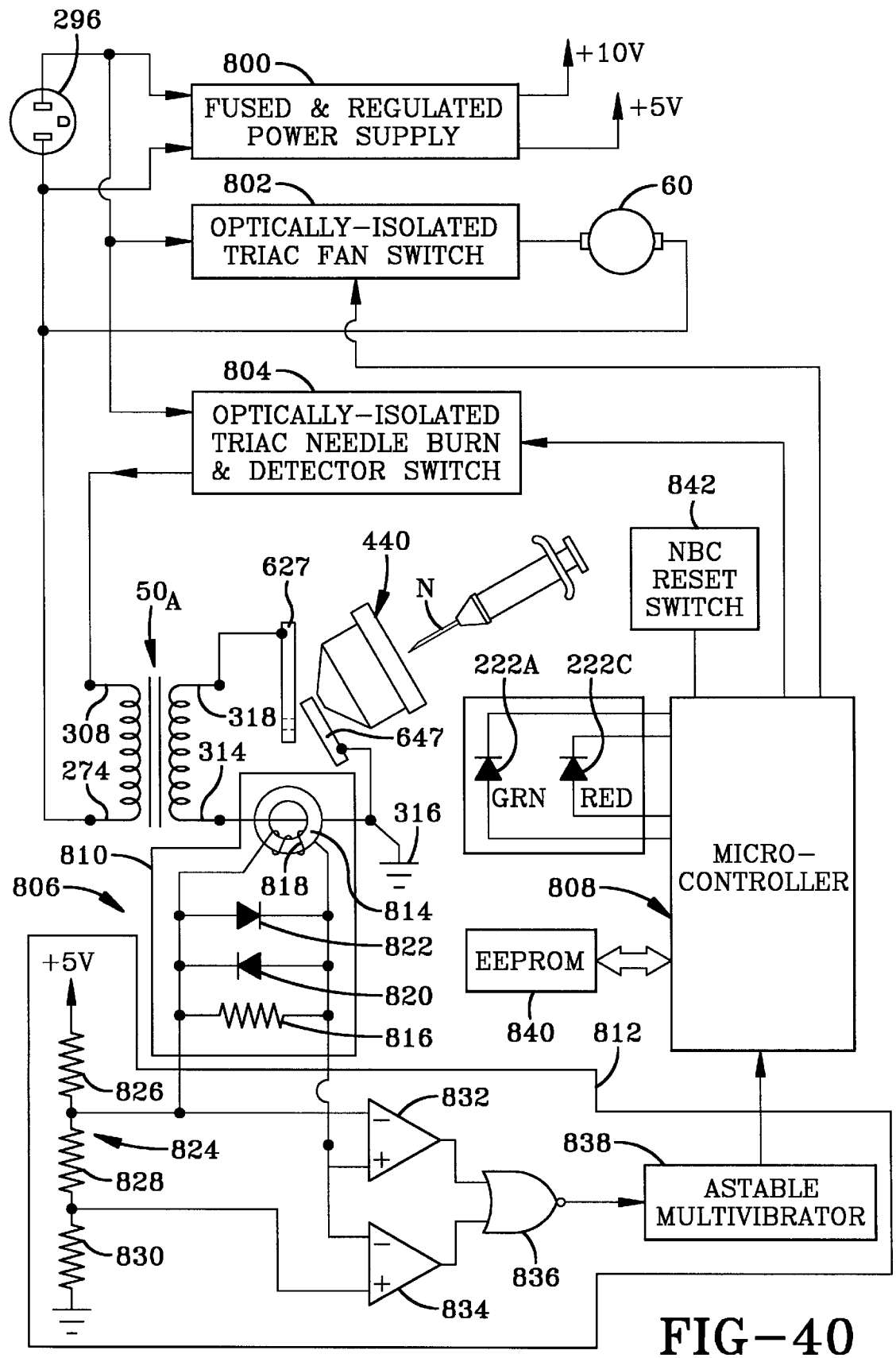
FIG. 40 is a circuit diagram, shown in partial block and partial schematic forms, for a preferred alternative mode of the circuitry in which current is monitored to detect the presence of a soiled hypodermic needle for destruction; and, FIG. 41 is a top level flow chart of an exemplary series of steps performed by the circuitry shown in FIG. 40.

FIG. 40 presents a circuit diagram, in partial block and partial schematic forms, of a preferred, alternative mode of the circuitry having an AC power source. This circuitry embodiment monitors current to detect the presence of a soiled hypodermic needle for destruction, unlike the circuitry of FIG. 21, which monitors voltage. The skilled artisan will appreciate that any signal characteristic related to the presence of a soiled hypodermic needle for destruction may be utilized to detect the same, and circuitry capable of monitoring for the selected signal characteristic are within the scope of the present invention.

The circuitry of FIG. 40 broadly includes connection to a power source such as by conventional AC power plug 296, a suitable power supply 800 furnishing the necessary circuitry voltages preferably in a fused and regulated manner, a switch 802 for selectively operating the fan motor 60, a switch 804 for selectively operating the needle bum transformer $50_A$ and a needle detection circuit 806, and a processor such as microcontroller 808 and related circuitry.

One of ordinary skill will appreciate that switches 802 and 804 may have a variety of configurations well-known for interfacing a semiconductor based processor to line voltage AC power peripherals. Although not depicted in detail in FIG. 40, one such configuration employs a semiconductor, optically-isolated switch in which a triac like a MAC228 Series triac commercially available from Motorola, Inc. of Schaumburg, Ill., U.S.A, selectively furnishes AC power to fan motor 60 (in the case of switch 802) and the needle burn transformer $50_A$ and a needle detection circuit 806 (in the case of switch 804). The triac in each switch may be driven by the output from a random-phase optoisolator triac driver, such as a Motorola MOC3021 Series Triac Driver, which in turn is operated by a control signal from microcontroller 808.

Needle detection circuit 806 broadly includes a current sensor circuit 810 for monitoring the presence and magnitude of needle burn current and generating an electrical signal a characteristic of which is related to the presence and magnitude of needle burn current, and a bidirectional AC current detection circuit 812 for receiving the electrical signal from current sensor circuit 810 and generating a control signal suitable for input into microcontroller 808. Current sensor circuit 810 may include a suitable toroidal current transformer (CT) 814 having the conductor electrically connecting tap 314 at the secondary side of transformer $50_A$ to first electrode 647 passing through its core, a loading resistor 816 electrically connected across the output of the CT coil winding 818, and two current limiting diodes 820 and 822 electrically connected in opposing orientations across the output of CT coil winding 818.

Current detection circuit 812 may include a voltage divider network 824 to form the signal source for the control signal suitable for input into microcontroller 808. Voltage divider network 824 may include three resistance segments or resistors 826, 828, 830, electrically connected in series between a DC power source of appropriate voltage, such as +5 Volts with the exemplary components described herein, and ground. The node between resistors 824 and 826 is electrically connected to the noninverting input of a first differential input operational amplifier 832. The node between resistors 826 and 830 is electrically connected to the inverting input of a second differential input operational amplifier 834. One side of the CT coil winding 818 is electrically connected to the inverting input of operational amplifier 834; the other side is electrically connected to both the noninverting input of operational amplifier 832 and the inverting input of operational amplifier 834. The outputs from operational amplifiers 832 and 834 are electrically connected to a two-input NOR gate 836, whose output is in turn electrically connected to an astable multivibrator 838. The output of astable multivibrator 838, which may be also referred to as one-shot 838, is electrically connected to and received by an input port of microcontroller 808.

Figure 41:
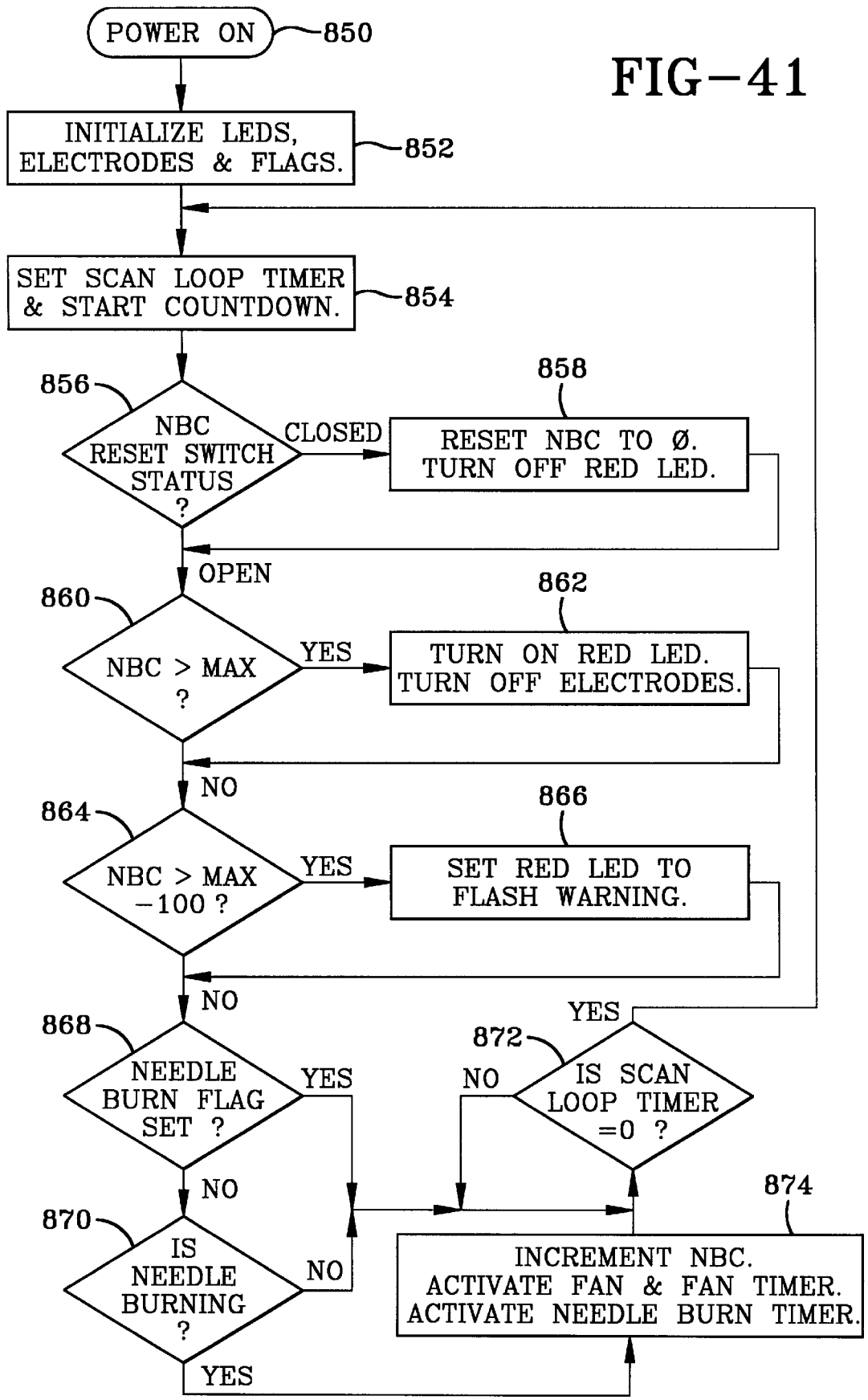

The processor chosen for use in the circuitry of FIG. 40 is preferably of compact, low power design having a sufficient extent of on-board non-volatile memory to store the flag and counter values utilized by a program executing the steps set forth in the exemplary top-level flow chart depicted in FIG. 41. One suitable processor is the CMOS single-chip 8-bit microcontroller Model 83C750 manufactured by Philips Electronics North America Corporation of New York, N.Y., U.S.A A non-volatile memory 840, such as a Model ST93C06 serial access CMOS 256 bit EEPROM manufactured by SGS-Thompson Microelectronics, Inc. of Carrollton, Tex., U.S.A, is provided for storage of the program, and is electrically connected to microcontroller 808.

The Model 83C750 microcontroller 808 includes a plurality of input/output ports with internal pull-up resistors, two of which are employed for electrical connection to green power indicator LED 222A, and red cartridge fill indicator LED 222C. In the embodiment of FIG. 40 green LED 222A is illuminated whenever power is available to apparatus 10, red LED 222C is illuminated whenever the cartridge is full (ie., the maximum number of needles N have been destroyed), and red LED 222C is illuminated intermittently (ie., flashes) whenever the cartridge is nearly full (ie., the number of needles N that has been destroyed is a preselected quantity such as 100 less than the preselected maximum quantity). Another input port of microcontroller 808 is electrically connected to a needle burn count (NBC) reset switch 842. NBC reset switch 842 is interlocked to cartridge 416 so as to monitor the presence of cartridge 416 and indicate when cartridge 416 has been replaced.

FIG. 41 shows a top-level flow chart of an exemplary program for the embodiment illustrated in FIG. 40. After power is turned on in step 850, the circuitry is initialized in step 852 with green LED 222A turned on and red LED 222C turned off, needle burn and detector switch 804 closed to furnish power to the electrodes, and the software flags and counters noted hereinafter set.

The status of apparatus 10 is checked completely every preselected time interval, such as 20 ms. In step 854 the count in a scan loop timer is set to furnish a countdown for the preselected 20 ms interval, and the countdown is begun. Next, in step 856 the current status of NBC reset switch 842 is checked. If cartridge 416 is present and properly secured within apparatus 10, switch 842 is open and the program continues; if not, in step 858 a counter that tracts the number of needles that have been destroyed by apparatus 10 since replacement of cartridge 416 is reset, such as to a count of zero, and red LED 222C is turned off.

The needle burn count is checked in step 860 to see if the preselected maximum number of needles have been destroyed. If not, the program continues. However, if so, in step 862 cartridge 416 is at capacity and red LED 222C is turned on continuously and power to the electrodes is turned off.

If the preselected maximum number of needles has not been destroyed the needle burn count is checked in step 864 to see if the cartridge 416 is nearly full by testing if the current needle burn count exceeds the preselected quantity such as 100 less than the preselected maximum quantity. If not, the program continues. However, if so, in step 866 the red LED 222C is set to flash, thereby warning the user of the impending need to replace cartridge 416.

In order to insure that an ongoing needle destruction process is not interrupted, a software flag is set whenever a needle is being destroyed. In step 868 the flag status is checked; if not, a test is conducted in step 870 to ascertain if a needle destruction has just begun. If the needle burn flag is found to be set when checked in step 868, the scan loop timer is next checked in step 872 to see if the present 20 ms apparatus 10 check interval has expired (ie., if the scan loop timer has count down to zero). If the present interval has expired, the entire process is repeated beginning with step 854. If the present interval has not expired, the scan loop timer is repeatedly checked until it has expired.

If a needle is not presently being destroyed when checked in step 870, the program proceeds with testing for expiration of the scan loop timer interval in step 872 as previously noted. However, if a needle is found to be in the process of destruction when check in step 870, the needle burn count is incremented, the fan and fan timer are activated for a preset period of time, and the needle burn flag is set and a needle burn timer activated for a preset period of time.

Conclusion

Even though a preferred and several alternative and modified structural embodiments of my present invention, which are operated by virtue of an AC power source, are disclosed, it is to be clearly understood that the same is susceptible to numerous changes apparent to one skilled in the art. Therefore, the scope of the present invention is not to be limited to the details shown and described but is intended to include all changes and modifications which come within the scope of the appended claims.

As should now be apparent, the present invention teaches a novel and unique apparatus for the electrical destruction of medical instruments in the nature of hypodermic needles and otherwise accomplishes the objects of the invention.

We claim:

1. An apparatus for the electrical destruction of medical instruments comprising:

a primary sub-housing;

a cartridge sub-housing demountably secured to said primary sub-housing;

first and second electrodes disposed within said cartridge sub-housing;

guide means incorporated in said cartridge sub-housing for accepting a medical instrument for destruction;

said first electrode being fixedly positioned with respect to said guide means;

said first electrode having a relatively hard deflection controlling tip;

a chordal surface on said deflection controlling tip;

a planar ramping surface on said deflection controlling tip intersecting said chordal surface;

said guide means directing said medical instrument such that insertion thereof in said guide means directs said medical instrument against said deflection controlling tip as well as against said second electrode to effect an electrical connection between said first and second electrodes;

means for moving said second electrode between fixed limits; and, means for providing a sufficient level of electrical energy to cause the electrical destruction of a medical instrument positioned in electrical contact with said first and second electrodes.

2. An apparatus for the electrical destruction of medical instruments, as set forth in claim 1, further comprising:

a supporting wall in said cartridge sub-housing; and, means to mount said first and second electrodes on said supporting wall.

3. An apparatus for the electrical destruction of medical instruments, as set forth in claim 2, wherein:

said second electrode is movable within a single plane;

said first electrode is fixed to receive medical instruments along a predetermined axis;

said predetermined axis of said first electrode is oriented at approximately 45° with respect to the plane within which said second electrode is movable.

4. An apparatus for the electrical destruction of medical instruments, as set forth in claim 1, further comprising:

a rear wall in said cartridge sub-housing;

a filter receiving recess incorporated in said rear wall;

a flow passage extending through said rear wall to communicate with said filter receiving recess;

a filter pack received within said recess.

5. An apparatus for the electrical destruction of medical instruments, as set forth in claim 4, further comprising:

a carbon filter; and, an environmental protection filter adjacent said carbon filter.

6. An apparatus for the electrical destruction of medical instruments, as set forth in claim 4, wherein:

said filter receiving recess is circumscribed by a peripheral wall;

a container is adapted to be received within said filter receiving recess;

said container has an inlet communicating with the interior of said cartridge sub-housing;

said container also opens into the interior of said primary sub-housing;

a carbon filter is located adjacent to said inlet; and, an environmental filter is located adjacent said carbon filter.

7. An apparatus for the electrical destruction of medical instruments, as set forth in claim 4, further comprising:

a fast-make electrical connection between said sub-housings;

a receiving blade mounted on said rear wall; and, spring clips mounted from said primary sub-housing.

8. An apparatus for the electrical destruction of medical instruments, as set forth in claim 1, wherein:

said second electrode is movable within a single plane;

second first electrode is fixed to receive medical instruments along predetermined axis;

said predetermined axis of said first electrode is oriented at approximately 45° with respect to the plane within which said second electrode is movable.

9. An apparatus for the electrical destruction of medical instruments, as set forth in claim 1, wherein:

said deflection controlling tip is made of carbide.

10. An apparatus for the electrical destruction of medical instruments, as set forth in claim 1, further comprising:

a protective cap assembly mounted in said guide means;

said protective cap assembly having flexible guard portions which meet at an apex and which flex to admit the medical instrument and generally comport to the exterior configuration of that portion of the medical instrument through the apex of said guard portions.

11. An apparatus for the electrical destruction of medical instruments, as set forth in claim 10, wherein:

said cartridge sub-housing presents a frontal wall;

a cup-shaped recess in said frontal wall;

said cup-shaped recess having a first annular wall that extends inwardly from said frontal wall to terminate in a seating a locating means;

a second, annular wall concentrically disposed radially inwardly with respect to said first annular wall;

said protective cap assembly having an outer ring portion with radially inner and radially outer perimeters;

said flexible guard portions extending from the radially inner perimeter of said ring portion;

a skirt portion presented from the radially outer perimeter of said ring portions;

said skirt portion disposed between said first and second annular walls of said cup-shaped recess when said protective cap assembly is mounted on said cartridge sub-housing.

12. An apparatus for the electrical destruction of medical instruments, as set forth in claim 11, further comprising:

means to secure said skirt portions between said concentric first and second annular walls.

13. An apparatus for the electrical destruction of medical instruments, as set forth in claim 12, wherein said means to secure said skirt portions between said concentric first and second annular walls comprises:

a retaining flange extending radially inwardly from said second annular wall; and, a detent notch incised radially within at least that skirt portion disposed adjacent to said second annular wall.

14. An apparatus for the electrical destruction of medical instruments, as set forth in claim 13, wherein:

said second, annular wall and said adjacent skirt portion incorporate radial discontinuities to facilitate insertion of said retaining flange within said detent notch.

15. An apparatus for the electrical destruction of medical instruments, as set forth in claim 1, further comprising:

a protective cap assembly mounted in said guide means;

said protective cap assembly having at least two nested members;

a plurality of flexible cuspids being successively supported circumferentially of each said nested member;

each said cuspid having lateral edges which meet at an apex; and, said lateral edges on successive cuspids are laterally contiguous.

16. An apparatus for the electrical destruction of medical instruments, as set forth in claim 15, wherein:

said nested members are disposed, one with respect to the other to avoid alignment between said lateral edges of the cuspids on said successively adjacent nested members.

17. An apparatus for the electrical destruction of medical instruments, as set forth in claim 16, further comprising:

means to maintain said cuspids on successively adjacent nested members out of alignment.

18. An apparatus for the electrical destruction of medical instruments, as set forth in claim 1, further comprising:

a hinge member presented from one said sub-housing operatively to engage guide means incorporated in said other sub-housing;

a latch member extending axially outwardly from one said sub-housing operatively to engage a locking bridge presented from the other said sub-housing.

19. An apparatus for the electrical destruction of medical instruments, as set forth in claim 18, wherein said hinge member further comprises:

opposed and spaced guide surfaces presented from said primary sub-housing;

a rigid, generally arcuate hinge member extending downwardly and rearwardly from said cartridge sub-housing to engage and be slidably received between said guide surfaces.

20. An apparatus for the electrical destruction of medical instruments, as set forth in claim 18, wherein:

said latch member has a cantilevered portion having flexural elasticity and terminating in a hooked catch;

said latch member extends outwardly and rearwardly in generally parallel relation to the base plate of said cartridge sub-housing;

said hooked catch has an inboard, planar face extending substantially perpendicularly from said cantilevered portion and an inclined outboard face;

said locking bridge has a planar outboard face to be engaged by said planar face on said hooked catch; and, said locking bridge also has a beveled surface to interact with said inclined outboard face on said hooked catch.

21. An apparatus for the electrical destruction of medical instruments, as set forth in claim 1, further comprising:

means for generating an electrical signal one characteristic of which is related to said electrical connection between said first and second electrodes; and, means for monitoring said characteristic of said electrical signal and detecting when said electrical connection between said first and second electrodes is effected.

22. An apparatus for the electrical destruction of medical instruments, as set forth in claim 21, further comprising means for inhibiting the electrical destruction of medical instruments after a preselected quantity of medical instruments has been destroyed.

* * * * *